US009315789B2

(12) United States Patent
Bieniarz et al.

(10) Patent No.: US 9,315,789 B2
(45) Date of Patent: *Apr. 19, 2016

(54) ANTIBODY CONJUGATES

(71) Applicant: Ventana Medical Systems, Inc., Tucson, AZ (US)

(72) Inventors: Christopher Bieniarz, Tucson, AZ (US); Jennifer Wong, San Ramon, CA (US); Mark Lefever, Oro Valley, AZ (US); Jerome W. Kosmeder, II, Tucson, AZ (US); Julia Ashworth-Sharpe, Tucson, AZ (US); Casey A. Kernag, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 126 days.

This patent is subject to a terminal disclaimer.

(21) Appl. No.: 14/146,389

(22) Filed: Jan. 2, 2014

(65) Prior Publication Data

US 2014/0147906 A1  May 29, 2014

Related U.S. Application Data

(60) Continuation of application No. 12/381,638, filed on Mar. 13, 2009, now Pat. No. 8,658,389, which is a division of application No. 11/413,418, filed on Apr. 27, 2006, now abandoned.

(60) Provisional application No. 60/675,759, filed on Apr. 28, 2005.

(51) Int. Cl.
*G01N 33/535* (2006.01)
*G01N 33/53* (2006.01)
*C12N 9/16* (2006.01)
*A61K 47/48* (2006.01)
*C07K 16/42* (2006.01)
*C07K 16/44* (2006.01)
*C12N 9/08* (2006.01)

(52) U.S. Cl.
CPC ............... *C12N 9/16* (2013.01); *A61K 47/4843* (2013.01); *A61K 47/48338* (2013.01); *C07K 16/42* (2013.01); *C07K 16/44* (2013.01); *C12N 9/0065* (2013.01); *G01N 33/535* (2013.01)

(58) Field of Classification Search
CPC ........... A61K 49/0058; A61K 47/4843; A61K 47/48338; A61K 47/48723; A61K 47/48384; G01N 33/535; C07K 14/44
See application file for complete search history.

(56) References Cited

U.S. PATENT DOCUMENTS

| 3,654,090 A | 4/1972 | Schuurs et al. |
| 3,839,153 A | 10/1974 | Schuurs et al. |
| 4,002,532 A | 1/1977 | Weltman et al. |
| 4,016,043 A | 4/1977 | Schuurs et al. |
| 4,101,380 A | 7/1978 | Rubinstein et al. |
| 4,182,695 A | 1/1980 | Horn et al. |
| 4,200,436 A | 4/1980 | Mochida et al. |
| 4,218,539 A | 8/1980 | Weltman |
| 4,232,119 A | 11/1980 | Carlsson et al. |
| 4,235,960 A | 11/1980 | Sasse et al. |
| 4,433,059 A | 2/1984 | Chang et al. |
| 4,454,226 A | 6/1984 | Ali et al. |
| 4,657,853 A | 4/1987 | Freytag et al. |
| 4,671,958 A | 6/1987 | Rodwell et al. |
| 4,732,863 A | 3/1988 | Tomasi et al. |
| 4,810,638 A | 3/1989 | Albarella et al. |
| 4,994,385 A | 2/1991 | Bieniarz et al. |
| 5,002,883 A | 3/1991 | Bieniarz et al. |
| 5,053,520 A | 10/1991 | Bieniarz et al. |
| 5,057,313 A | 10/1991 | Shih et al. |
| 5,063,109 A | 11/1991 | Bieniarz et al. |
| 5,191,066 A | 3/1993 | Bieniarz et al. |
| 5,648,218 A | 7/1997 | Stults |
| 5,759,808 A | 6/1998 | Casterman et al. |
| 5,789,219 A | 8/1998 | Bieniarz et al. |
| 5,800,988 A | 9/1998 | Casterman et al. |
| 5,840,526 A | 11/1998 | Casterman et al. |
| 5,874,541 A | 2/1999 | Casterman et al. |
| 5,989,842 A | 11/1999 | Schmidt et al. |

(Continued)

FOREIGN PATENT DOCUMENTS

EP  0903152  3/1999
EP  0990903  4/2000

(Continued)

OTHER PUBLICATIONS

Akerblom et al., "Preparation and characterization of conjugates of monoclonal antibodies and *Staphylococcal enterotoxin* A using a new hydrophilic cross-linker," *Bioconjugate Chem.* 4:6(455-466, Nov.-Dec. 1993 (abstract only).
Aldwin et al., "A water-soluble, monitorable peptide and protein crosslinking agent," *Anal. Biochem.* 164(2):494-501, Aug. 1, 1987 (abstract only).
Anderson et al., "Polymer modification of antibody to eliminate immune complex and Fc binding," *Journal of Immunological Methods* 109:37-42, 1988.
Anderson et al., "Improved fluoroimmunoassay using the dye Alexa Fluor 647 with the RAPTOR, a fiber optic biosensor," *Journal of Immunological Methods* 271:17-24, 2002.
Annunziato et al., "p-maleimidophenyl isocyanate: a novel heterobifunctional linker for hydroxyl to thiol coupling," *Bioconjugate Chem.* 4(3):212-218, May-Jun. 1993 (abstract only).

(Continued)

*Primary Examiner* — Shafiqul Haq
(74) *Attorney, Agent, or Firm* — Charney IP Law LLC; Thomas M. Finetti

(57) ABSTRACT

Antibody/signal-generating moiety conjugates are disclosed that include an antibody covalently linked to a signal-generating moiety through a heterobifunctional polyalkyleneglycol linker. The disclosed conjugates show exceptional signal-generation in immunohistochemical and in situ hybridization assays on tissue sections and cytology samples. In one embodiment, enzyme-metallographic detection of nucleic acid sequences with hapten-labeled probes can be accomplished using the disclosed conjugates as a primary antibody without amplification.

12 Claims, 22 Drawing Sheets

(56) References Cited

U.S. PATENT DOCUMENTS

| | | | |
|---|---|---|---|
| 6,005,079 A | 12/1999 | Casterman et al. | |
| 6,015,695 A | 1/2000 | Casterman et al. | |
| 6,057,429 A | 5/2000 | Bieniarz et al. | |
| 6,124,435 A | 9/2000 | Ashkenazi et al. | |
| 6,160,153 A | 12/2000 | Bieniarz et al. | |
| 6,218,160 B1 | 4/2001 | Duan | |
| 6,252,053 B1 | 6/2001 | Ohbayashi et al. | |
| 6,537,519 B2 | 3/2003 | Borel et al. | |
| 6,576,746 B2 | 6/2003 | McBride et al. | |
| 6,613,564 B2 | 9/2003 | Ohbayashi et al. | |
| 6,630,307 B2 | 10/2003 | Bruchez et al. | |
| 6,649,138 B2 | 11/2003 | Adams et al. | |
| 6,670,113 B2 | 12/2003 | Hainfeld | |
| 6,682,596 B2 | 1/2004 | Zehnder et al. | |
| 6,800,728 B2 | 10/2004 | Schwartz | |
| 6,815,064 B2 | 11/2004 | Treadway et al. | |
| 8,658,389 B2 * | 2/2014 | Bieniarz et al. | 435/7.9 |
| 2004/0002146 A1 | 1/2004 | Ohbayashi et al. | |
| 2004/0115165 A1 | 6/2004 | Rosen et al. | |
| 2004/0265922 A1 | 12/2004 | Bieniarz et al. | |
| 2005/0012182 A1 | 1/2005 | Jang et al. | |
| 2005/0074499 A1 | 4/2005 | Tagawa et al. | |
| 2005/0100976 A1 | 5/2005 | Bieniarz et al. | |
| 2005/0158770 A1 | 7/2005 | Bieniarz et al. | |
| 2005/0186642 A1 | 8/2005 | Tacha | |
| 2006/0020134 A1 | 1/2006 | Davis et al. | |
| 2006/0246523 A1 | 11/2006 | Bieniarz et al. | |
| 2006/0246524 A1 | 11/2006 | Bauer et al. | |
| 2007/0117153 A1 | 5/2007 | Bieniarz et al. | |
| 2007/0122408 A1 | 5/2007 | Barbas, II | |
| 2009/0181398 A1 | 7/2009 | Bauer et al. | |

FOREIGN PATENT DOCUMENTS

| | | |
|---|---|---|
| EP | 1118335 | 7/2001 |
| EP | 1170018 | 9/2002 |
| GB | 782420 | 9/1957 |
| JP | 05-304987 | 11/1993 |
| WO | WO 90/10621 | 9/1990 |
| WO | WO 92/07268 | 4/1992 |
| WO | WO 00/54807 | 9/2000 |
| WO | WO 01/12154 | 2/2001 |
| WO | WO 03/031464 | 4/2003 |
| WO | WO 03/072017 | 9/2003 |
| WO | WO 2004/024889 | 3/2004 |
| WO | WO 2004/081053 | 9/2004 |
| WO | WO 2005/001889 | 1/2005 |
| WO | WO 2005/003777 | 1/2005 |
| WO | WO 2006/036646 | 4/2006 |

OTHER PUBLICATIONS

Ansell et al., "3-(2-Pyridyldithio)propionic Acid Hydrazide as a Cross-Linker in the Formation of Liposome-Antibody Conjugates," *Bioconjugate Chem.* 7(4):490-496, Jul.-Aug. 1996.

Arpicco et al., "New coupling reagents for the preparation of disulfide cross-linked conjugates with increased stability," *Bioconjugate Chem.* 8(3):327-337, May-Jun. 1997 (abstract only).

Atkinson et al., "Potential Antiradiation Drugs. I. Amide, Hydroxamic Acid, and Hydrazine Derivatives of Mercapto Acids. Amino Thioacids," *Journal of Medicinal Chemistry, American Chemical Society* 8:29-33, Jan. 1965.

Bernatowicz et al., "The N-hydroxysuccinimide ester of Boc[S-(3-nitro-2-pyridinesulfenyl)]-cysteine: a heterobifunctional cross linking agent," *Biochem. Biophys. Res. Commun.* 132(3):1046-1050, Nov. 15, 1985 (abstract only).

Bieniarz et al., "Extended Length Heterobifunctional Coupling Agents for Protein Conjugation," *Bioconjugate Chem.* 7(1):88-95, Jan.-Feb. 1996.

Bieniarz et al., "Thermally Stabilized Immunoconjugates: Conjugation of Antibodies to Alkaline Phosphatase Stabilized with Polymeric Cross-Linkers," *Bioconjugate Chem.* 9(3):399-402, May-Jun. 1998.

Bieniarz et al., "Alkaline phosphatase activatable polymeric cross-linkers and their use in the stabilization of proteins," *Bioconjugate Chem.* 9(3):390-398, May-Jun. 1998 (abstract only).

Capel et al., "The Effect of 2-Mercaptoethanol on IgM and IgG Antibody Activity," *Journal of Immunological Methods* 36(1):77-80, 1980.

Carlsson et al., "Protein thiolation and reversible protein-protein conjugation, N Succinimidyl 3-s(pyridyldithio)proprionate, a new heterobifunctional reagent," *Biochem. J.* 173(3):723-737, Sep. 1, 1978 (abstract only).

Carroll et al., "Enhanced stability in vitro and in vivo of immunoconjugates prepared with 5-methyl-2-iminothiolane," *Bioconjugate Chem.* 5(3):248-256, May-Jun. 1994 (abstract only).

Chamow et al., "Conjugation of Soluble CD4 without Loss of Biological Activity via a Novel Carbohydrate-directed Cross-linking Reagent," *The Journal of Biological Chemistry* 267(22):15916-15922, Aug. 5, 1992.

Chan et al., "Quantum Dot Bioconjugates for Ultrasensitive Nonisotopic Detection," *Science* 281(5385):2016-2018, Sep. 25, 1998.

Chen et al., "The use of bifunctional polyethyleneglycol derivatives for coupling of proteins to and cross-linking of collagen matrices," *J. Mater Sci. Mater Med.* 13(11):1029-1035, Nov. 2002 (abstract only).

Chong et al., "A new heterobifunctional cross-linking reagent for the study of biological interactions between proteins. I. Design, synthesis, and characterization," *J. Biol. Chem.* 256(10):5064-5070, May 25, 1981 (abstract only).

Collioud et al., "Oriented and covalent immobilization of target molecules to solid supports: synthesis and application of a light-activatable and thiol-reactive cross-linking reagent," *Bioconjugate Chem.* 4(6):528-536, Nov.-Dec. 1993 (abstract only).

Cunningham-Rundles et al., "Biological activities of polyethylene-glycol immunoglobulin conjugates. Resistance to enzymatic degradation," *Journal of Immunological Methods* 152:177-190, 1992.

del Rosario et al., "Sulfhydryl Site-Specific Cross-linking and Labeling of Monoclonal Antibodies by a Fluorescent Equilibrium Transfer Alkylation Cross-Link Reagent," *Bioconjugate Chem.* 1(1):51-59, Jan.-Feb. 1990.

Dhawan, "Design and construction of novel molecular conjugates for signal amplification (1): conjugation of multiple horseradish peroxidase molecules to immunoglobulin via primary amines on lysine peptide chains," *Peptides* 23:2091-2098, 2002.

Duncan et al., "A new reagent which may be used to introduce sulfhydryl groups into proteins, and its use in the preparation of conjugates for immunoassays," *Anal. Biochem.* 132(1):68-73, Jul. 1, 1983 (abstract only).

Fischer-Durand et al., "Synthesis of Metal-Carbonyl-Dendrimer-Antibody Immunoconjugates: Towards a New Format for Carbonyl Metallo Immunoassay," *Chem. Bio. Chem.* 5:519-525, 2004.

Frisch et al., "Synthesis of short polyoxyethylene-based heterobifunctional cross-linking reagents. Application to the coupling of peptides to liposomes," *Bioconjugate Chem.* 7(2):180-186, Mar.-Apr. 1996 (abstract only).

Fu et al., "Carbohydrate-directed conjugation of cobra venom factor to antibody by selective derivatization of the terminal galactose residues," *Bioconjugate Chem.* 12(2):271-279, Mar.-Apr. 2001 (abstract only).

Heindel et al., "A Novel Heterobifunctional Linker for Formyl to Thiol Coupling," *Bioconjugate Chem.* 2(6):427-430, Nov.-Dec. 1991.

Hermanson, *Bioconjugate Techniques*, pp. 71-76, Academic Press, 1996.

Hinman et al., "Preparation and Characterization of Monoclonal Antibody Conjugates of the Calicheamicins: A Novel and Potent Family of Antitumor Antibiotics," *Cancer Research* 53:3336-3342, Jul. 15, 1993.

Husain et al., "Fc Site-Specific Labeling of Immunoglobulins with Calf Intestinal Alkaline Phosphatase," *Bioconjugate Chem.* 5(5):482-490, Sep.-Oct. 1994.

Huwyler et al., "Receptor Mediated Delivery of Daunomycin Using Immunoliposomes: Pharmacokinetics and Tissue Distribution in the Rat," *J. Pharmacol Exp Ther*, 282(3):1541-1546, 1997.

Jeanson et al., "Preparation of reproducible alkaline phosphatase-antibody conjugates for enzyme immunoassay using a heterobifunctional linking agent," *Anal. Biochem.* 172(2):392-396, Aug. 1, 1988 (abstract only).

(56) References Cited

OTHER PUBLICATIONS

Jou et al., "Monoclonal antibodies and a heterobifunctional reagent: a novel approach to the vectorial labeling of selected membrane proteins," *Immunol. Commun.* 11(1):357-375, 1982 (abstract only).
Kaiser et al., "Basic studies on heterobifunctional biotin-PEG conjugates with 3-(4-pyridyldithio)propionyl marker on the second terminus," *Bioconjugate Chem.* 8(4):545-551, Jul.-Aug. 1997 (abstract only).
Kortt et al., "Dimeric and trimeric antibodies: high avidity scFvs for cancer targeting," *Biomol. Eng.* 18(3):95-108, Oct. 15, 2001 (abstract only).
Kossaczka et al., "Synthesis and immunological Properties of Vi and Di-O-Acetyl Pectin Protein Conjugates with Adipic Acid Dihydrazide as the Linker," *Infection and Immunity* 65(6):2088-2093, Jun. 1997.
Lee et al., "Efficient coupling of glycopeptides to proteins with a heterobifunctional reagent," *Biochemistry* 28(4):1856-1861, Feb. 21, 1989 (abstract only).
Liberatore et al., "Heterobifunctional cross-linking of a monoclonal antibody with 2-methyl-N1-benzenesulfonyl-N4-bromoacetylquinonediimide," *Biochem. Biophys. Res. Commun.* 158(3):640-645, Feb. 15, 1989 (abstract only).
Liberatore et al., "Site-directed chemical modification and cross-linking of a monoclonal antibody using equilibrium transfer alkylating cross-link reagents," *Bioconjugate Chem.* 1(1):36-50, Jan.-Feb. 1990.
Liu et al., "Synthesis, Stability, and Cellular Internalization of Gold Nanoparticles Containing Mixed Peptide-Poly(ethylene glycol) Monolayers," *Anal. Chem.* 79(6):2221-2229, Mar. 15, 2007.
Maassen et al., "Synthesis and Application of Two Reagents for the Introduction of Sulfhydryl Groups into Proteins," *Eur. J. Biochem.* 134:327-330, 1983.
Mason et al., "Alkaline phosphatase and peroxidase for double immunoenzymatic labeling of cellular constituents," *J. Clin. Pathol.* 31:454-460, 1978.
Matsuya et al., "A core-shell type fluorescent nanosphere processing reactive pol (ethylene glycol) tethered chains on the surface for zeptomole detection of protein in time-resolved fluorometric immunoassay," *Anal. Chem.* 75(22):6124-6132, Nov. 15, 2003 (abstract only).
Mendintz et al., "Quantum dot bioconjugates for imaging, labeling and sensing," *Nature Materials* 4:435-446, Jun. 2005.
Nakane et al., "Peroxidase-labeled antibody a new method of conjugation," *The Journal of Histochemistry and Cytochemistry* 22(12):1084-1091, 1974.
O'Shannessy et al., "Specific Conjugation Reactions of Oligosaccharide Moieties of Immunoglobulins," *Journal of Applied Biochemistry* 7(4-5):347-355, Aug.-Oct. 1985.
O'Shannessy et al., "Labeling of the oligosaccharide moieties of immunoglobulins," *Journal of Immunological Methods* 99(2):153-161, May 20, 1987.
O'Sullivan et al., "Enzyme immunoassay: a review," *Annals of Clinical Biochemistry* 16:221:240, 1979.
Park et al., "Immunoliposomes Sandwich Fluorometric Assay (ILSF) for Detection of *Escherichia coli* 0157:H7," *Journal of Food Science* 69(6):M151-M156, 2004.
Pasut et al., "Protein, peptide and non-peptide drug PEGylation for therapeutic application," *Expert Opinion on Therapeutic Patents* 14(6):859-894, 2004.

Peeters et al., "Comparison of four bifunctional reagents for coupling peptides to proteins and the effect of the three moieties on the immunogenicity of the conjugates," *Journal of Immunological Methods* 120:133-143, 1989.
Quanta Biodesign Catalogue, Nov. 5, 2004 (31 pages).
Roberts et al., "Chemistry for peptide and protein PEGylation," *Advanced Drug Delivery Reviews* 54:459-476, 2002.
Shafer et al., "Activation of Soluble Polysaccharides with 1-Cyano-4-Dimethylaminopyridinium Tetrafluoroborate (CDAP) for use in Protein-Polysaccharide Conjugate Vaccines and Immunological Reagents. II. Selective Crosslinking of Proteins to CDAP-Activated Polysaccharides," *Vaccine* 18:1273-1281, 2000.
Simons et al., "Novel cross-linked enzyme-antibody conjugates for Western blot and ELISA," *Journal of Immunological Methods* 315:88-98, 2006.
Taylor et al., "A Thiolation Reagent for Cell Surface Carbohydrate," *Biochemistry International* 1(4):353-358, Oct. 21, 1980.
Uyeda et al., "Design of Water-Soluble Quantum Dots with Novel Surface Ligands for Biological Applications," *Mat. Res. Soc. Symp. Proc.* vol. 789, 6 pages, 2004.
Veronese, "Peptide and protein PEGylation: a review of problems and solutions," *Biomaterials* 22:405-417, 2001.
Vogel, "Preparation of immunoconjugates using antibody oligosaccharide moieties," *Methods Mol. Biol.* 283:87-108, 2004.
Wilchek et al., "Labeling Glycoconjugates with Hydrazide Reagents," *Methods in Enzymology* 138:429-442, 1987.
Yan et al., "N-hydroxysuccinimide ester functionalized perfluorophenyl azides as novel photoactive heterobifunctional cross-linking reagents. The covalent immobilization of biomolecules to polymer surfaces," *Bioconjugate Chem.* 5(2):151-157, Mar.-Apr. 1994 (abstract only).
Zalipsky et al., "Evaluation of a new reagent for covalent attachment of polyethylene glycol to proteins," *Biotechnol. Appl. Biochem.* 15(1):100-114, Feb. 1992 (abstract only).
Zara et al., "A Carbohydrate-Directed Heterobifunctional Cross-Linking Reagent for the Synthesis of Immunoconjugates," *Anal. Biochemistry* 194:156-162, 1991.
Office action issued May 6, 2010, by the European Patent Office for related European Application No. 06838327.2, filed Nov. 21, 2006, 8 pages.
Office action issued Oct. 26, 2010, by the European Patent Office for related European patent application No. 06758689.1, filed Apr. 27, 2006, 12 pages.
Office action issued Apr. 5, 2011, by the Australian Patent Office for related Australian Application No. 2006318438, filed Nov. 21, 2006, 2 pages.
Office action issued Jul. 20, 2011, by the Chinese Patent Office for related Chinese Application No. 200680043958.2, filed Nov. 21, 2006, 11 pages (English-language translation).
Office action issued Aug. 9, 2011, from the Japanese Patent Office for related Japanese Application No. 2008-509141, filed Apr. 27, 2006, 6 pages (English-language translation).
Office action issued Feb. 7, 2012, by the Japanese Patent Office for related Japanese Application No. 2008-542455, filed Nov. 21, 2006, 7 pages (English-language translation).
Office Action issued Jun. 4, 2012, by the Canadian Patent Office for related Canadian Application No. 2,609,702, filed Apr. 27, 2006, 7 pages.
Notice of Reasons for Rejection issued Jun. 19, 2012, by the Japanese Patent Office for related Japanese Patent Application No. 2008-542455, filed Apr. 27, 2006, 5 pages (English-language translation).

* cited by examiner

ANTIBODY CONJUGATES

RELATED APPLICATION DATA

This is a continuation of U.S. patent application Ser. No. 12/381,638, filed Mar. 13, 2009, which is a divisional of U.S. patent application Ser. No. 11/413,418, filed Apr. 27, 2006, now abandoned, which claims the benefit of U.S. Provisional Patent Application No. 60/675,759, filed Apr. 28, 2005, which applications are incorporated by reference herein.

BACKGROUND OF THE INVENTION

1. Field

The present invention relates to reagents and methods for detecting a molecule of interest in a biological sample. More particularly, the present invention relates to antibody conjugates and methods for using such conjugates to detect a molecule of interest in a biological sample such as a tissue section.

2. Background

Covalent conjugates of antibodies and signal-generating moieties can be used in immunoassays for detecting specific target molecules in biological samples. The antibody portion of such conjugates specifically binds to a target in the sample and the signal-generating moiety is utilized to provide a detectable signal that indicates the presence/and or location of the target. One type of conjugate that has become widely used, especially for immunohistochemical analysis, is a conjugate of an antibody and an enzyme (antibody-enzyme conjugate). A detectable signal is generated by adding a substrate to the sample and the enzyme portion of the conjugate converts the substrate to, for example, a colored, fluorescent or luminescent product at the site where the antibody portion is bound to its target.

Antibody-enzyme conjugates are typically prepared using polyfunctional (typically bifunctional) coupling reagents that are characterized by having at least two reactive groups, one of which is reacted with a functional group on the antibody and the other of which is reacted with a functional group on the enzyme. However, coupling can lead to inactivation of either or both of the antibody and the enzyme due to steric effects or because the coupling reagents react with functional groups located on portions of the enzyme or antibody that are critical for their function or specificity.

An approach to minimizing loss of antibody specificity and enzyme activity is to use a coupling scheme that is specific to particular amino acid residues on either or both of the antibody and the enzyme that are not associated with their functions. This approach is exemplified by the method for Fc-specific conjugation as described in U.S. Pat. No. 5,191,066, which is incorporated by reference herein. In this method, sulfhydryl groups (thiol groups) are introduced specifically to a glycosylated region of the Fc portion of an antibody and used along with a linker molecule to covalently attach an enzyme to the antibody. Since the Fc portion is not involved with the specific binding properties of the antibody, such conjugates retain greater specificity, which increases the detectable signal for a particular target molecule of interest and lowers background due to non-specific binding.

Although site specific conjugation can be used to help minimize loss of antibody specificity and enzyme activity due to loss of critical functional groups, such methods do not address loss of antibody specificity and enzyme activity that arise from steric effects such as those steric effects due to aggregation of multiple conjugates and from interactions between the antibody and the enzyme(s) in a conjugate. Detrimental steric effects also can arise due to unintended cross-linking between multiple enzymes, antibodies and/or conjugates, which occurs during preparation of a conjugate composition.

One approach to minimizing loss of antibody specificity and enzyme activity due to steric effects is to increase the length of the coupling reagent in order that the antibody and enzyme are separated by a greater distance. This approach is exemplified by the methods and conjugation reagents disclosed in U.S. Pat. No. 5,053,520. In this method, heterobifunctional linkers having extended alkyl, cycloalkyl, alkylcycloalkyl and aromatic portions are used to couple an antibody to an enzyme(s). Although such linkers contain more atoms and should provide greater separation between an antibody and an enzyme(s), it is believed that the hydrophobic nature of such linkers increases detrimental aggregation of conjugates in aqueous solution due to hydrophobic effects. In addition, such linkers are flexible enough to permit detrimental intra-conjugate interactions between the antibody and the enzyme(s) as a conjugate collapses in on itself to minimize its size due to hydrophobic effects.

An attempt to minimize detrimental aggregation between conjugates is described in U.S. Pat. No. 4,810,638, which describes the use of homo-bifunctional, bis-maleimidopolyalkylene glycol linkers to prepare antibody-enzyme conjugates. However, use of such homo-bifunctional linkers can lead to cross-linking of antibodies, enzymes and/or conjugates during preparation of the conjugates. Cross-linking increases the average size and counteracts to some extent the increased water solubility imparted by using the glycol linker. Furthermore, cross-linking leads to lower monodispersity in a conjugate composition, which can have detrimental effects on consistency of results, especially in tissue and cell samples where detection of a target with a conjugate may be limited by diffusion through cell membranes.

Some heterobifunctional polyethylene glycol linkers are known, but there are no known attempts to use them as coupling reagents for forming antibody-enzyme conjugates. Rather, as disclosed in Chen et al. (Chen et al., "The use of bifunctional polyethylene glycol derivatives for coupling of proteins to and cross-linking of collagen matrices," J. Mater. Sci. Mater. Med., 13: 1029-1035, 2002), such agents have been utilized to prepare degradable matrices to which active proteins are linked for the purposes of tissue engineering.

From the standpoint of increasing the signal generated by a given antibody conjugate it is desirable to conjugate multiple enzymes to a single antibody. However, as the number of enzymes linked to a single antibody increases, the likelihood increases that conjugate function will be impaired for steric reasons due to crowding of multiple enzymes around the single antibody. One approach to minimizing crowding of enzymes is to employ a scaffold to provide separation between enzymes and between enzymes and antibodies or antibody fragments. U.S. Pat. Nos. 6,252,053 and 6,613,564, for example, describe the use of polylysine or dextran scaffolds to increase separation between enzymes, while still effectively increasing the number of enzyme molecules per specific binding component [specifically F(ab')$_2$ fragments]. While the approach described in these patents does increase the average number of signal-generating moieties per specific-binding component, the use of a polymeric scaffold (typically of low monodispersity) increases background and decreases reproducibility. The high molecular weight (typically greater >1 MDa) of such constructs can hinder diffusion and tissue/cell penetrability is diminished, thereby reducing signal.

What is needed, therefore, is an antibody/signal-generating conjugate composition that overcomes at least the described limitations of prior approaches. In particular, antibody conjugates of enzyme (and methods of making the same) that are smaller and yet retain the high signal generating capacity of larger scaffolded conjugates are desirable.

SUMMARY OF THE INVENTION

Antibody conjugates with signal generating moieties are disclosed, as are methods for making and using the conjugates. The disclosed antibody conjugates exhibit superior performance for detection of molecules of interest in biological samples, especially for detection of such molecules in tissue sections and cytology samples. In particular, disclosed antibody-enzyme conjugates retain high amounts of antibody specificity and enzymatic activity, and thereby provide more intense staining with less background than conjugates currently used for detection of antigens in biological samples.

In one aspect, a conjugate is disclosed that includes an antibody covalently linked to a signal-generating moiety through a heterobifunctional polyalkyleneglycol linker such as a heterobifunctional polyethyleneglycol (PEG) linker. In one embodiment, a disclosed conjugate includes an antibody and a signal-generating moiety covalently linked by a heterobifunctional PEG linker that includes a combination of two different reactive groups selected from a carbonyl-reactive group, an amine-reactive group, a thiol-reactive group and a photo-reactive group. In particular embodiments, the PEG linker includes a combination of a thiol reactive group and an amine-reactive group or a combination of a carbonyl-reactive group and a thiol-reactive group. In more particular embodiments, the thiol reactive group includes a maleimide group, the amine reactive group includes an active ester and the carbonyl-reactive group includes a hydrazine derivative.

In even more particular embodiments, the disclosed conjugate has the general formula:

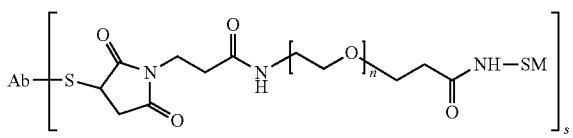

wherein Ab is an antibody, SM is a signal-generating moiety (for example, an enzyme) and n=1 to 50 (such as n=2 to 30, n=2 to 20 or n=4 to 12) and s=1 to 10 (such as s=2 to 6 or s=3 to 4).

In other even more particular embodiments, a disclosed conjugate has the formula:

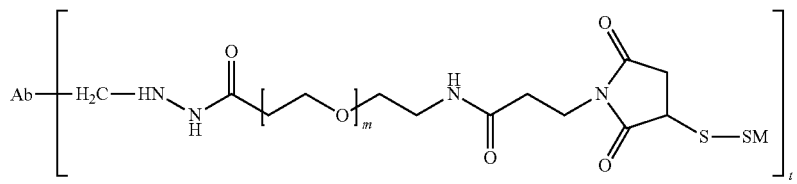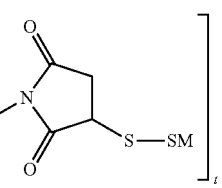

wherein Ab is an antibody, SM is a signal-generating moiety (such as an enzyme, m=1 to 50 (such as m=2 to 30, m=2 to 20 or m=4 to 12) and t=1 to 10 (such as t=2 to 6 or t=3 to 4). In some instances, the hydrazide group of the PEG linker is bonded to the carbon of an aldehyde group formed in the glycosylated portion of the antibody by oxidation.

In another aspect, methods for making the disclosed conjugates are provided. In one embodiment a method of making an antibody conjugate includes forming a thiolated antibody from an antibody; reacting a signal-generating moiety having an amine group with a PEG maleimide/active ester bifunctional linker to form an activated signal-generating moiety; and reacting the thiolated antibody with the activated signal-generating moiety to form the conjugate of the antibody and the signal-generating moiety. The thiolated antibody can be formed by reduction of intrinsic cystine bridges of the antibody with a reductant or can be formed by reacting the antibody with a reagent that introduces a thiol to the antibody.

In another embodiment, a method for making a disclosed antibody conjugate includes reacting an antibody with an oxidant to form an aldehyde-bearing antibody; reacting the aldehyde-bearing antibody with a PEG maleimide/hydrazide bifunctional linker to form a thiol-reactive antibody; and reacting the thiol-reactive antibody with a thiolated signal-generating moiety to form the antibody-signal-generating moiety conjugate. In a particular embodiment, reacting the antibody with an oxidant to form the aldehyde-bearing antibody includes oxidizing (such as with periodate, bromine or iodine) a glycosylated region of the antibody to form the aldehyde-bearing antibody.

In another aspect, PEG maleimide/hydrazide bifunctional linkers are disclosed that can be used in the disclosed methods to provide disclosed conjugates. In yet another aspect, methods are disclosed for detecting molecules in biological samples using disclosed conjugates. These and additional aspects, embodiments and features of the disclosure will become apparent from the detailed description and examples that follow.

DETAILED DESCRIPTION OF SEVERAL ILLUSTRATIVE EMBODIMENTS

Figure 1A:
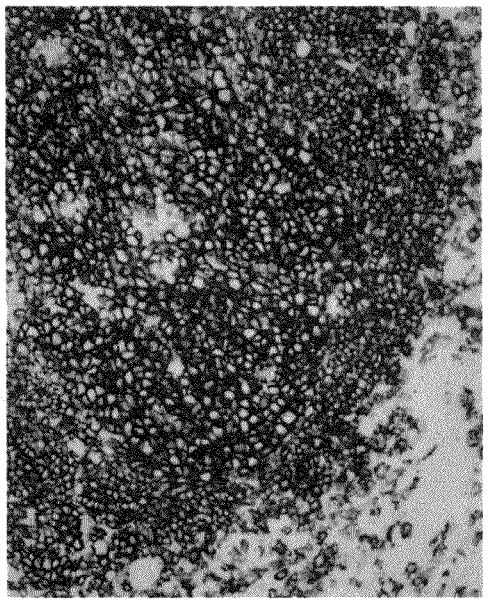
FIGS. 1A-1D are images of tissue sections immunohistochemically stained for Ki67 with a disclosed conjugate, in comparison to a scaffolded conjugate, both before and after storage at 45° C. for 7 days.

Further aspects of the invention are illustrated by the following non-limiting examples, which proceed with respect to the abbreviations and terms defined below.

I. Abbreviations
2-ME—2-mercaptoethanol
2-MEA—2-mercaptoethylamine
Ab—antibody
ALP—alkaline phosphatase
BSA—bovine serum albumin
DTE—dithioerythritol (cis-2,3-dihydroxy-1,4-dithiolbutane)
DTT—dithiothreitol (trans-2,3-dihydroxy-1,4-dithiolbutane)
EGFR—epidermal growth factor receptor
ER—estrogen receptor
HRP—horseradish peroxidase
IHC—immunohistochemistry
ISH—in situ hybridization
MAL—maleimide
NHS—N-hydroxy-succinimide
PEG—polyethylene glycol
PR—progesterone receptor
SAMSA—S-Acetylmercaptosuccinic acid
SATA—N-succinimidyl S-acetylthioacetate
SATP—Succinimidyl acetyl-thiopropionate
SM—signal-generating moiety
SMPT—Succinimidyloxycarbonyl-α-methyl-α-(2-pyridyldithio)toluene
SPDP—N-Succinimidyl 3-(2-pyridyldithio)propionate
TCEP—tris(carboxyethyl)phosphine II. Terms The terms "a," "an" and "the" include both singular and plural referents unless the context clearly indicates otherwise.

The term "antibody" collectively refers to immunoglobulins or immunoglobulin-like molecules (including IgA, IgD, IgE, IgG and IgM, combinations thereof, and similar molecules produced during an immune response in any vertebrate, for example, in mammals such as humans, goats, rats, rabbits and mice) and antibody fragments that specifically bind to a molecule of interest (or a group of highly similar molecules of interest) to the substantial exclusion of binding to other molecules (for example, antibodies and antibody fragments that have a binding constant for the molecule of interest that is at least $10^3$ $M^{-1}$ greater, $10^4$ $M^{-1}$ greater or $10^5$ $M^{-1}$ greater than a binding constant for other molecules in a biological sample). Antibody fragments include proteolytic antibody fragments [such as $F(ab')_2$ fragments, Fab' fragments, Fab'-SH fragments and Fab fragments as are known in the art], recombinant antibody fragments (such as sFv fragments, dsFv fragments, bispecific sFv fragments, bispecific dsFv fragments, diabodies, and triabodies as are known in the art), and camelid antibodies (see, for example, U.S. Pat. Nos. 6,015,695; 6,005,079; 5,874,541; 5,840,526; 5,800,988; and 5,759,808).

The phrase "molecule of interest" refers to a molecule for which the presence, location and/or concentration is to be determined. Examples of molecules of interest include proteins and nucleic acid sequences labeled with haptens.

III. Overview

In one aspect, an antibody/signal-generating moiety conjugate is disclosed that includes an antibody covalently linked to a signal-generating moiety through a heterobifunctional polyalkyleneglycol linker having the general structure shown below:

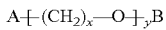

wherein A and B include different reactive groups, x is an integer from 2 to 10 (such as 2, 3 or 4), and y is an integer from 1 to 50, for example, from 2 to 30 such as from 3 to 20 or from 4 to 12. One or more hydrogen atoms can be substituted for additional functional groups such as hydroxyl groups, alkoxy groups (such as methoxy and ethoxy), halogen atoms (F, Cl, Br, I), sulfato groups and amino groups (including mono- and di-substituted amino groups such as dialkyl amino groups).

A and B of the linker can independently include a carbonyl-reactive group, an amine-reactive group, a thiol-reactive group or a photo-reactive group, but are not the same. Examples of carbonyl-reactive groups include aldehyde- and ketone-reactive groups like hydrazine derivatives and amines. Examples of amine-reactive groups include active esters such as NHS or sulfo-NHS, isothiocyanates, isocyanates, acyl azides, sulfonyl chlorides, aldehydes, glyoxals, epoxides, oxiranes, carbonates, aryl halides, imidoesters, anhydrides and the like. Examples of thiol-reactive groups include non-polymerizable Michael acceptors, haloacetyl groups (such as iodoacetyl), alkyl halides, maleimides, aziridines, acryloyl groups, vinyl sulfones, benzoquinones, aromatic groups that can undergo nucleophilic substitution such as fluorobenzene groups (such as tetra and pentafluorobenzene groups), and disulfide groups such as pyridyl disulfide groups and thiols activated with Ellman's reagent. Examples of photo-reactive groups include aryl azide and halogenated aryl azides. Additional examples of each of these types of groups will be apparent to those skilled in the art. Further examples and information regarding reaction conditions and methods for exchanging one type of reactive group for another are provided in Hermanson, "Bioconjugate Techniques," Academic Press, San Diego, 1996, which is incorporated by reference herein. In a particular embodiment, a thiol-reactive group is other than vinyl sulfone.

In some embodiments, a thiol-reactive group of the heterobifunctional linker is covalently linked to the antibody and an amine-reactive group of the heterobifunctional linker is covalently linked to the signal-generating moiety, or vice versa. For example, a thiol-reactive group of the heterobifunctional linker can be covalently linked to a cysteine residue (such as formed by reduction of a cystine bridge) of the antibody or a thiol-reactive group of the heterobifunctional linker can be covalently linked to a thiol group that is introduced to the antibody, and the amine-reactive group is covalently linked to the signal-generating moiety.

Alternatively, an aldehyde-reactive group of the heterobifunctional linker can be covalently linked to the antibody and an amine-reactive group of the heterobifunctional linker can be covalently linked to the signal-generating moiety, or vice versa. In a particular embodiment, an aldehyde-reactive group of the heterobifunctional linker can be covalently linked to an aldehyde formed on a glycosylated portion of an antibody, and the amine-reactive group is covalently linked to the signal-generating moiety.

In yet other embodiments, an aldehyde-reactive group of the heterobifunctional linker is covalently linked to the antibody and a thiol-reactive group of the heterobifunctional linker is covalently linked to the signal-generating moiety, or vice versa.

Examples of signal-generating moieties include enzymes (such as horseradish peroxidase, alkaline phosphatase, acid phosphatase, glucose oxidase, β-galactosidase, β-glucuronidase or β-lactamase), fluorescent molecules (such as fluoresceins, coumarins, BODIPY dyes, resorufins, and rhodamines; additional examples can be found in *The Handbook—A Guide to Fluorescent Probes and Labeling Technologies*, Invitrogen Corporation, Eugene, Oreg.), detectable constructs (such as fluorescent constructs like quantum dots, which can be obtained, for example, from Invitrogen Corporation, Eugene, Oreg.; see, for example, U.S. Pat. Nos. 6,815,064, 6,682,596 and 6,649,138, each of which patents is incorporated by reference herein), metal chelates (such as DOTA and DPTA chelates of radioactive or paramagnetic metal ions like $Gd^{3+}$) and liposomes (such as liposomes sequestering fluorescent molecules).

When the signal-generating moiety includes an enzyme, a chromagenic compound, fluorogenic compound, or luminogenic compound is used in combination with the enzyme to generate a detectable signal (A wide variety of such compounds are available, for example, from Molecular Probes, Inc., Eugene Oreg.). Particular examples of chromogenic compounds include di-aminobenzidine (DAB), 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue and tetrazolium violet.

In particular embodiments the heterobifunctional linker of the conjugate has the formula:

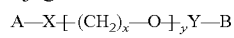

wherein A and B include different reactive groups as before, x and y are as before, and X and Y are spacer groups, for example, spacer groups having between 1 and 10 carbons such as between 1 and 6 carbons or between 1 and 4 carbons, and optionally containing one or more amide linkages, ether linkages, ester linkages and the like. Spacers X and Y can be the same or different, and can be straight-chained, branched or cyclic (for example, aliphatic or aromatic cyclic structures), and can be unsubstituted or substituted. Functional groups that can be substituents on a spacer include carbonyl groups, hydroxyl groups, halogen (F, Cl, Br and I) atoms, alkoxy groups (such as methoxy and ethoxy), nitro groups, and sulfato groups.

In other particular embodiments, the heterobifunctional linker is a heterobifunctional polyethylene glycol linker having the formula:

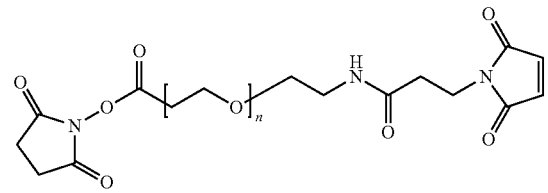

wherein n=1 to 50, for example, n=2 to 30 such as n=3 to 20 or n=4 to 12. In more particular embodiments, a carbonyl of a succinimide group of this linker is covalently linked to an amine group on the signal-generating moiety and a maleimide group of the linker is covalently linked to a thiol group of the antibody, or vice versa. In other more particular embodiments, an average of between about 1 and about 10 signal moieties are covalently linked to an antibody.

In some particular embodiments, the heterobifunctional linker has the formula:

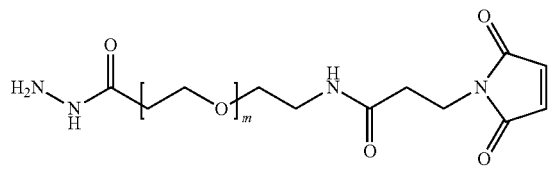

wherein m=1 to 50, for example, m=2 to 30 such as m=3 to 20 or 4 to 12. In some more particular embodiments, a hydrazide group of the linker is covalently linked to a aldehyde group of the antibody and a maleimide group of the linker is covalently linked to a thiol group of the signal-generating moiety, or vice versa. In even more particular embodiments, the aldehyde group of the antibody is an aldehyde group formed in an Fc portion of the antibody by oxidation of a glycosylated region of the Fc portion of the antibody. In still other more particular embodiments, an average of between about 1 and about 10 signal-generating moieties are covalently linked to the antibody, such signal-generating moieties including enzymes, quantum dots and liposomes.

In other particular embodiments, a heterobifunctional PEG-linked antibody-signal-generating moiety conjugate comprises a conjugate having the formula:

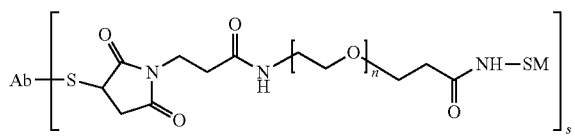

wherein Ab is an antibody, SM is a signal-generating moiety and n=1 to 50 (such as n=n=2 to 30, n=2 to 20 or n=4 to 12) and s=1 to 10 (such as s=2 to 6 or s=3 to 4).

In still other embodiments, a heterobifunctional PEG-linked antibody-signal-generating moiety conjugate comprises a conjugate having the formula:

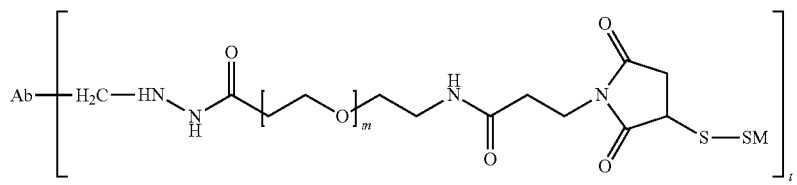

wherein Ab is an antibody, SM is a signal-generating moiety, m=1 to 50 (such as m=2 to 30, m=2 to 20 or m=4 to 12) and t=1 to 10 (such as t=2 to 6 or t=3 to 4).

Although the antibody used in the disclosed conjugates can specifically bind any particular molecule or particular group of highly similar molecules, in particular embodiments, the antibody comprises an anti-hapten antibody (which can be used to detect a hapten-labeled probe sequence directed to a nucleic acid sequence of interest) or an antibody the specifically binds to a particular protein or form of a particular protein (such as a phosphorylated form of a protein) that may be present in a sample. Haptens are small organic molecules that are specifically bound by antibodies, although by themselves they will not elicit an immune response in an animal and must first be linked to a larger carrier molecule such as a protein or a poly-nucleic acid to generate an immune response. Examples of haptens include di-nitrophenol, biotin, and digoxigenin. In still other particular embodiments, the antibody comprises an anti-antibody antibody that can be used as a secondary antibody in an immunoassay. For example, the antibody can comprise an anti-IgG antibody such as an anti-mouse IgG antibody, an anti-rabbit IgG antibody or an anti-goat IgG antibody.

The disclosed antibody conjugates can be utilized for detecting molecules of interest in any type of binding immunoassay, including immunohistochemical binding assays. In one embodiment, the disclosed conjugates are used as a labeled primary antibody in an immunoassay, for example, a primary antibody directed to a particular molecule or a hapten-labeled molecule. Or, where the molecule of interest is multi-epitopic a mixture of conjugates directed to the multiple epitopes can be used. In another embodiment, the disclosed conjugates are used as secondary antibodies in an immunoassay (for example, directed to a primary antibody that binds the molecule of interest; the molecule of interest can be bound by two primary antibodies in a sandwich-type assay when multi-epitopic). In yet another embodiment, mixtures of disclosed conjugates are used to provide further amplification of a signal due to a molecule of interest bound by a primary antibody (the molecule of interest can be bound by two primary antibodies in a sandwich-type assay). For example, a first conjugate in a mixture is directed to a primary antibody that binds a molecule of interest and a second conjugate is directed to the antibody portion of the first conjugate, thereby localizing more signal-generating moieties at the site of the molecule of interest. Other types of assays in which the disclosed conjugates can be used are readily apparent to those skilled in the art.

In another aspect, a heterobifunctional linker is disclosed having the formula:

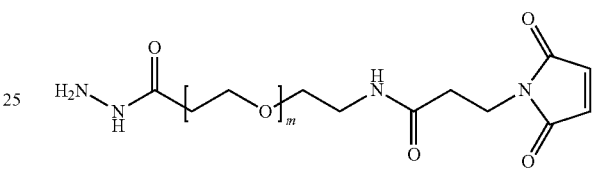

wherein m=1 to 50, for example, m=2 to 30 such as m=3 to 20 or m=4 to 12.

In yet another aspect, a method is disclosed for preparing an antibody-signal-generating moiety conjugate, the method including forming a thiolated antibody from an antibody; reacting a signal-generating moiety having an amine group with a PEG maleimide/active ester bifunctional linker to form an activated signal-generating moiety; and reacting the thiolated antibody with the activated signal-generating moiety to form the antibody-signal-generating moiety conjugate. A thiolated antibody can be formed by reacting the antibody with a reducing agent to form the thiolated antibody, for example, by reacting the antibody with a reducing agent to form a thiolated antibody having an average number of thiols per antibody of between about 1 and about 10. The average number of thiols per antibody can be determined by titration. Examples of reducing agents include reducing agents selected from the group consisting of 2-mercaptoethanol, 2-mercaptoethylamine, DTT, DTE and TCEP, and combinations thereof. In a particular embodiment the reducing agent is selected from the group consisting of DTT and DTE, and combinations thereof, and used at a concentration of between about 1 mM and about 40 mM.

Alternatively, forming the thiolated antibody includes introducing a thiol group to the antibody. For example, the thiol group can be introduced to the antibody by reaction with a reagent selected from the group consisting of 2-Iminothiolane, SATA, SATP, SPDP, N-Acetylhomocysteinethiolactone, SAMSA, and cystamine, and combinations thereof (see, for example, Hermanson, "Bioconjugate Techniques," Academic Press, San Diego, 1996, which is incorporated by reference herein). In a more particular embodiment, introducing the thiol group to the antibody includes reacting the antibody with an oxidant (such as periodate, $I_2$, $Br_2$, or a combination thereof) to convert a sugar moiety of the antibody into an aldehyde group and then reacting the aldehyde group with cystamine.

In other particular embodiments, reacting the signal-generating moiety with a PEG maleimide/active ester bifunctional linker to form an activated signal-generating moiety includes reacting the signal-generating moiety with a PEG maleimide/active ester having the formula:

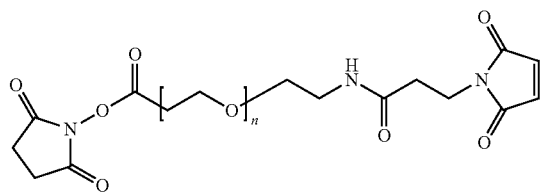

wherein n=1 to 50, for example, n=2 to 30 such as n=3 to 20 or n=4 to 12. The signal-generating moiety can, for example, be an enzyme (such as horseradish peroxidase or alkaline phosphatase).

In a further aspect, a method is disclosed for preparing an antibody-signal-generating moiety conjugate that includes reacting an antibody with an oxidant to form an aldehyde-bearing antibody; reacting the aldehyde-bearing antibody with a PEG maleimide/hydrazide bifunctional linker to form a thiol-reactive antibody; and reacting the thiol-reactive antibody with a thiolated signal-generating moiety to form the antibody-signal-generating moiety conjugate. In a particular embodiment, reacting the antibody with an oxidant to form the aldehyde-bearing antibody includes oxidizing (such as with periodate) a glycosylated region of the antibody to form the aldehyde-bearing antibody. In a more particular embodiment, reacting an antibody with an oxidant to form an aldehyde-bearing antibody includes introducing an average of between about 1 and about 10 aldehyde groups per antibody. In another more particular embodiment, the PEG maleimide/hydrazide bifunctional linker used in the method has the formula:

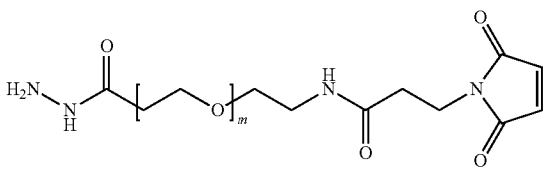

wherein m=1 to 50, for example, m=2 to 30 such as m=3 to 20 or m=4 to 12.

A thiolated signal-generating moiety can be formed from a signal-generating moiety by reacting the signal-generating moiety (such as an enzyme) with a reducing agent (such as a reducing agent selected from the group consisting of 2-mercaptoethanol, 2-mercaptoethylamine, DTT, DTE and TCEP, and combinations thereof) to form the thiolated signal-generating moiety, or by introducing a thiol group (for example, by reacting a signal generating moiety with a reagent selected from the group consisting of 2-Iminothiolane, SATA, SATP, SPDP, N-Acetylhomocysteinethiolactone, SAMSA, and cystamine, and combinations thereof).

In a still further aspect, a method is disclosed for detecting a molecule of interest in a biological sample that includes contacting the biological sample with a heterobifunctional PEG-linked antibody-signal-generating moiety conjugate and detecting a signal generated by the antibody-signal-generating moiety conjugate. The biological sample can be any sample containing biomolecules (such as proteins, nucleic acids, lipids, hormones etc.), but in particular embodiments, the biological sample includes a tissue section (such as obtained by biopsy) or a cytology sample (such as a Pap smear or blood smear). In a particular embodiment, the heterobifunctional PEG-linked antibody-signal-generating moiety conjugate includes an antibody covalently linked to an enzyme such as horseradish peroxidase or alkaline phophatase. In other particular embodiments, the heterobifunctional PEG-linked antibody-signal-generating moiety conjugate includes an antibody covalently linked to a detectable construct or a liposome.

In a more particular method, the signal-generating moiety comprises an enzyme such as alkaline phosphatase and the method further comprises contacting the biological sample with a water-soluble metal ion and a redox-inactive substrate of the enzyme that is converted to a redox-active agent by the enzyme, which redox-active agent reduces the metal ion causing it to precipitate. (see, for example, co-pending U.S. patent application Ser. No. 11/015,646, filed Dec. 20, 2004, PCT Publication No. 2005/003777 and U.S. Patent Application Publication No. 2004/0265922; each of which is incorporated by reference herein). In another particular embodiment the signal-generating moiety comprises an oxidoreductase enzyme (such as horseradish peroxidase) and the method further comprise contacting the biological sample with a water soluble metal ion, an oxidizing agent and a reducing agent (see, for example, U.S. Pat. No. 6,670,113, which is incorporated by reference herein).

IV. Examples

The following non-limiting examples are provided to further illustrate certain aspects of the invention.

A. Preparation of Antibody-Signal-Generating Moiety Conjugates Using Maleimide PEG Active Esters.

In one embodiment, a disclosed antibody signal-generating moiety conjugate is prepared according to the processes described in schemes 1 to 3 below, wherein the heterobifunctional polyalkylene glycol linker is a polyethylene glycol linker having an amine-reactive group (active ester) and a thiol-reactive group (maleimide). As shown in Scheme 1, a signal-generating moiety (such as an enzyme or a quantum dot) that has one or more available amine groups is reacted with an excess of the linker to form an activated signal-generating moiety.

Scheme 1

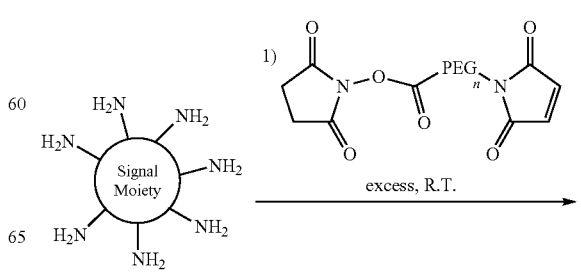

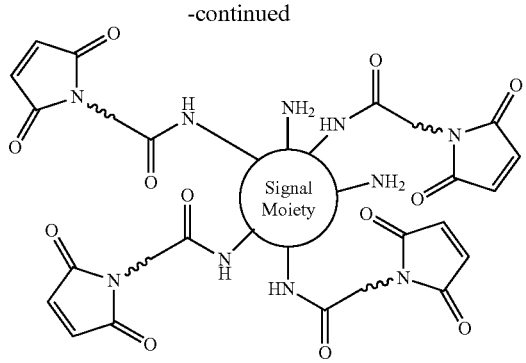

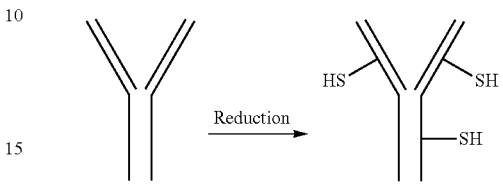

Scheme 2 example, a concentration of between about 5 mM and about 30 mM or between about 15 mM and about 25 mM) is utilized to introduce a limited number of thiols (such as between about 2 and about 6) to the antibody while keeping the antibody intact (which can be determined by size-exclusion chromatography).

Thiol groups are introduced to the antibody by treating the antibody with a reducing agent such as DTT as shown in Scheme 2. For a mild reducing agent such as DTE or DTT, a concentration of between about 1 mM and about 40 mM (for The components produced according to Schemes 1 and 2 are then combined to give a conjugate as shown in Scheme 3.

Scheme 3

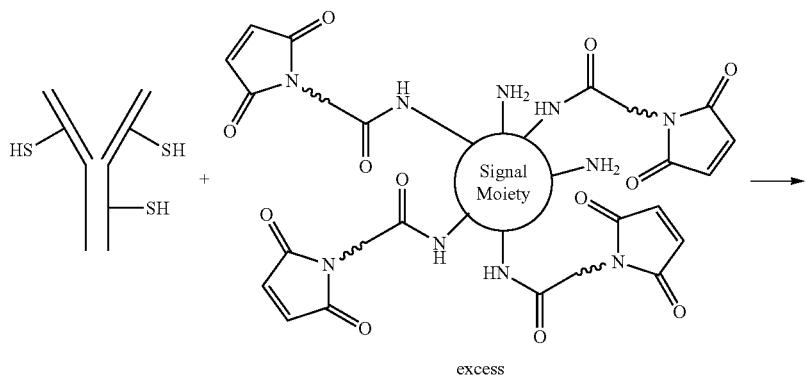

excess

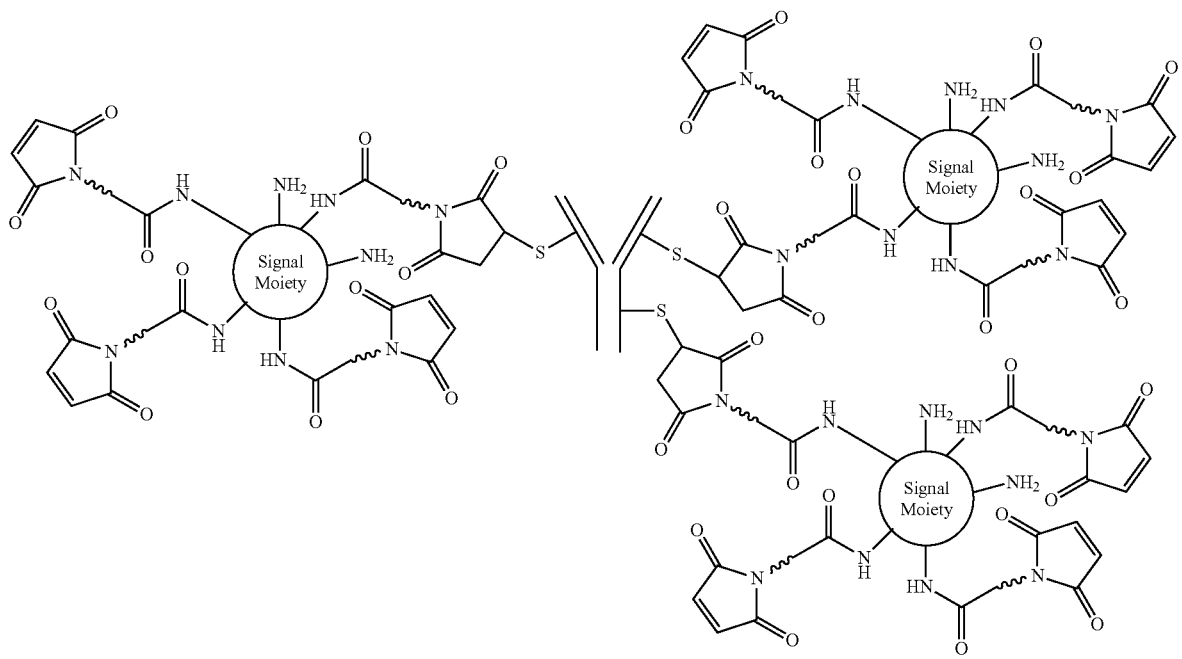

Although Schemes 1-3 illustrate an optimal process for maleimide PEG active esters, wherein the signal-generating moiety is first activated by reacting an amine group with the active ester of the linker to form an activated signal-generating moiety, it is also possible to first activate the antibody by reacting either an amine or a thiol on the antibody with the linker and then react the activated antibody with the signal generating moiety [having either a thiol or an amine to react with the remaining reactive group on the linker as appropriate]. Furthermore, although 3 signal-generating moieties are shown in Scheme 3, it is possible to link multiple antibodies to a single signal-generating moiety or any number of signal-generating moieties to a single antibody.

In an alternative embodiment, an antibody is activated for conjugation and then conjugated to a signal-generating moiety as shown in Schemes 4 and 5 below. In Scheme 4, the antibody is activated instead of the signal generating moiety as was shown in Scheme 1. In the particular embodiment of scheme 4, a sugar moiety (such as located in a glycosylated region of the Fc portion of the antibody) is first oxidized to provide an aldehyde group, which is then reacted with an aldehyde-reactive group of the linker (such as a hydrazide group of the illustrated maleimide/hydrazide PEG linker).

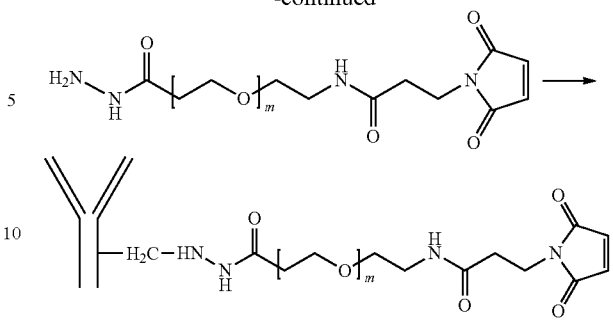

Then, as shown in Scheme 5, a thiol-reactive group of the linker portion of the activated antibody (such as a maleimide group as illustrated) is then reacted with a thiol group on the signal generating moiety. Again, the process can be reversed, wherein the linker is first reacted with an aldehyde group on the signal-generating moiety (formed, for example, by oxidation of a sugar moiety) to form an activated signal generating moiety, and then the activated signal generating moiety can be reacted with a thiol group on the antibody. Furthermore, although Schemes 4 and 5 show only a single linker joining a single antibody and a single signal-generating moiety, it is to be understood that it is also possible to link multiple signal generating moieties to a single antibody or to link several antibodies to a one signal-generating moiety.

Scheme 5

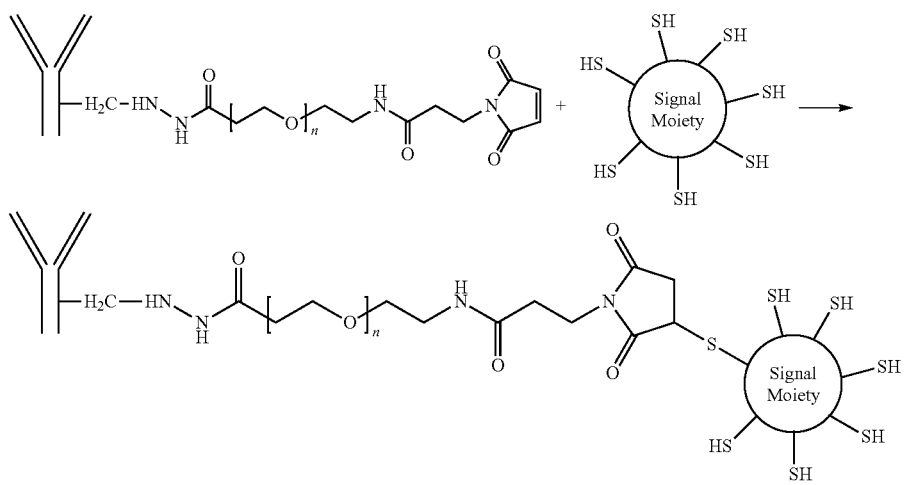

Scheme 4

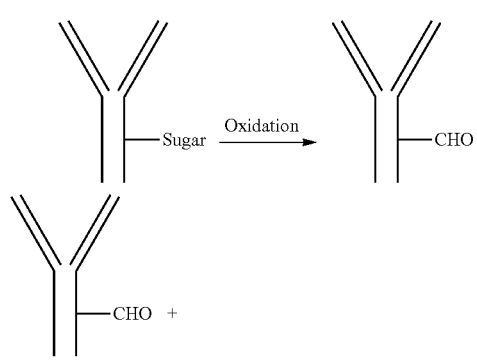

B. Preparation of Antibody-Horseradish Peroxidase Conjugates

Activation of HRP

HRP can, for example, be activated for conjugation by treatment with a 100-fold molar excess of a bifunctional PEG linker having a maleimide group and an active ester group (for example, the MAL-PEG$_4$-NHS, MAL-PEG$_S$-NHS or MAL-PEG$_{12}$-NHS linkers available from Quanta Biodesign, Powell, Ohio) at ambient temperature (23-25° C.) for 60 minutes. After purification across a Superdex 200 10/300 GL column, excess linker-free HRP, typically with five to seven maleimides, is obtained with a 100-fold molar excess. An exemplary procedure is outlined below for production of an HRP antibody conjugate using a MAL-PEG$_4$-NHS linker. The number of maleimide groups on an activated HRP can determined by the method described in detail in Example D.

HRP-PEG$_4$-maleimide (1): To a 4 mL amber vial was added 78.8 mg (100 eq.) of MAL-dPEG$_4$™ NHS ester (Quanta Biodesign, Powell, Ohio, F.W.=513.50), followed by 2.46 mL (61.5 mg, 1.53 μM) of HRP (Horseradish Peroxidase, Pierce, Rockford, Ill. Lot FJ925901) as a 25 mg/mL solution in 0.1 M sodium phosphate, pH 7.5. The vial was then placed on an autorotator in the dark at ambient temperature (23-25° C.), and the amide bond forming reaction was allowed to proceed for 1 hour. A 400 μl aliquot was then removed for purification, and the remainder of the solution was temporarily stored at 4° C. Pure HRP-PEG$_4$-maleimide was then obtained by fractionating the sample on an Akta Purifier fitted with a Superdex 10/300 column (Amersham, Piscataway, N.J.) eluted with 0.1 M sodium phosphate, pH 7.5 at 1.0 mL/min. The HRP containing fractions were pooled to give 2.0 ml of a 4.52 mg/mL solution of HRP-PEG$_4$-maleimide (90% recovery) as measured by UV/VIS spectrophotometry using an extinction coefficient at 280 nm of a 1% solution (pH 6.5) of 6.52.

Introduction of Thiols to Antibodies

To activate an antibody, for example, an anti-mouse IgG or anti-rabbit IgG antibody, for conjugation an antibody can be incubated with 25 mmol DTT at ambient temperature (23-25° C.) for 25 minutes. After purification across a PD-10 SE column, DTT-free antibody, typically with two to six free thiols, is obtained (Scheme 2). The exemplary procedure outlined for preparing goat anti-mouse IgG thiol is generally applicable to other antibodies. The number of thiols per antibody can be determined by the thiol assay described in Example D.

Goat Anti-Mouse IgG-Thiol (2): To a 8 mL amber vial was added 4.11 mL of Goat-anti-Mouse IgG (Bethyl, Montgomery, Tex.) as a 3.01 mg/mL solution in 0.1 M sodium phosphate, 1.0 mM EDTA, pH 6.5. To this solution was then added 216 μL of a freshly prepared 500 mM solution of the reducing agent DTT (1,4-Dithiothreitol, Sigma-Aldrich, St. Louis, Mo.). The vial was placed in the dark on an autorotator and the disulfide reduction was allowed to proceed for 25 minutes. The reaction solution was split into four equal volumes (due to the limited capacity of a desalting column used), and excess DTT was removed by passing each of the fractions across a PD-10 desalting column eluted with 0.1 M sodium phosphate, 1.0 mM EDTA, pH 6.5. The antibody containing fractions were combined to give 8.0 mL of a 1.22 mg/mL solution of DTT free Goat-anti-Mouse IgG-SH (78% recovery) as measured by UV/VIS spectrophotometry using an extinction coefficient at 280 nm of a 1% solution at pH 6.5 of 14.

HRP-Antibody Conjugation

To a thiolated antibody (such as anti-mouse IgG-thiol or anti-rabbit IgG-thiol), is added a three fold molar excess of HRP-PEG$_4$-maleimide. The reaction is then incubated at ambient temperature (23-25° C.) for 16 hours. After purification across a Superdex 200 10/300 GL SE column a conjugate, typically with an average of 2 or 3 HRPs per antibody, is obtained. The number of HRPs per antibody is determined by measuring the ratio of absorbances at 280 nm/403 nm of the conjugate, and performing the calculations outlined in section Example D. An exemplary procedure is outlined below.

HRP-PEG$_4$-Goat-Anti-Mouse IgG (3): To an 8 mL amber vial was added 4.0 mL of the Goat-anti-Mouse IgG-thiol solution (2) (1 eq., 4.88 mg, 0.0326 pimp and 864 μL of the HRP-PEG$_4$-maleimide solution (1) (3 eq., 3.91 mg, 0.0976 pimp. The vial was then placed on an autorotator in the dark at ambient temperature (23-25° C.), and the Michael addition was allowed to proceed for 16 hours. HRP-PEG$_4$-Goat-anti-Mouse IgG conjugate devoid of free antibody and free HRP was then obtained by fractionating the sample on an Akta Purifier fitted with a Superdex 10/300 column (Amersham, Piscatawy, N.J.) eluted with 0.1 M sodium phosphate, pH 7.5, at 0.9 ml/minute. After pooling fractions, 9.73 mL of a 1.04 mg/mL solution of conjugate was obtained as determined by Pierces' Coomasie Plus protein assay described in Example C. The conjugate was then stored in a cold room at 4° C. until use.

C. MW Characterization of Antibody/Enzyme Conjugates

To illustrate the superior monodispersity of the disclosed conjugates the MW profiles of a total of twelve examples of the disclosed conjugates (specifically, eight HRP-anti-mouse IgG conjugates and four HRP-anti-rabbit IgG conjugates) were determined by size-exclusion chromatography on an Akta Purifier fitted with a Superdex 200 10/300 GL column (Amersham, Piscatawy, N.J.) eluted with 0.1 M sodium phosphate buffer pH 7.5, 0.5-1.0 mL/min. Molecular weight calibration standards included: Aldolase (158 kDa), Catalase (232 kDa), Ferritin (440 kDa), Thyroglobin (669 kDa), Ribonuclease A (13.7 kDa), Chymotrypsinogen (25 kDa), Ovalbumin (43 kDa), and Albumin (67 kDa). The conjugates examined had an average MW between about 230 and about 330 kDa with an overall range of MWs for a given conjugate of approximately 190-550 kDa. Reinjection of purified conjugates demonstrated that conjugates were free of non-conjugated HRP and antibody.

D. Analytical Procedures for Determining Conjugate

The following representative methods may be used to determine maleimide and thiol content as well as the number of HRP molecules per conjugate.

Total Protein Microplate Procedure (Pierce)

Equipment and Materials:

| | |
|---|---|
| BSA | Pierce (Rockford, IL) |
| Coomasie Plus ™ Reagent | Pierce (Rockford, IL) |
| Microtiter plate | BIO-TEK Synergy HT |
| Plate reader | |

Procedure:

1. Turn on plate reader and let warm up for at least 30 minutes at 595 nm.
2. Prepare a set of BSA standards (1.0, 0.5, 0.25, and 0.125 mg/mL) in deionized water.
3. In triplicate, pipette 15 ml of the Blank, and each standard or unknown into the appropriate microplate wells.
4. Add 300 ml of the Coomasie Plus™ Reagent to each well and mix with the plate shaker for 30 seconds.
5. Remove the plate from the shaker. For the most consistent results, incubate plate for 10 minutes at room temperature.
6. Measure the absorbance at 595 nm with the plate reader.
7. Subtract the average 595 nm measurement for the Blank replicates from the 595 nm measurements of all other individual standard and unknown sample replicates (done automatically by plate reader).
8. Prepare a standard curve by plotting the average Blank-corrected 595 nm measurements for each BSA standard versus its concentration in μg/mL. Use the standard curve to determine the protein concentration of each unknown sample (done by plate reader).

Determination of Ab-Thiol and HRP-PEG$_4$-Maleimide Content

Equipment and Materials:

| Mercaptoethanol | J. T. Baker, Phillipsburg, NJ |
| Ellman's Reagent | Pierce, Rockford, IL |
| Sodium phosphate | |

EDTA

Materials Preparation:
Reaction Buffer: 0.1 M sodium phosphate; 1 mM EDTA, pH 8.0.
Mercaptoethanol (BME): M.W.=78.3, d=1.114 g/ml.
Procedure:
1. Turn on the plate reader and let warm up for at least 30 minutes at 412 nm.
2. Prepare working stock: 7 µl BME into 5 ml Reaction Buffer
3. In triplicate, prepare a set of BME standards as described below.

| Standard | Volume of Reaction buffer | | Final Conc. | |
|---|---|---|---|---|
| Standard stock | 900 µl | 100 µl of working stock | 2 | mM |
| Standard 1 | 500 µl | 500 µl of Standard stock | 1 | mM |
| Standard 2 | 500 µl | 500 µl of Standard 1 | 0.5 | mM |
| Standard 3 | 500 µl | 500 µl of Standard 2 | 0.25 | mM |
| Standard 4 | 500 µl | 500 µl of Standard 3 | 0.125 | mM |
| Standard 5 | 500 µl | 500 µl of Standard 4 | 0.0625 | mM |
| Standard 6 | 500 µl | 500 µl of Standard 5 | 0.03125 | mM |
| Standard 7 | 500 µl | 500 µl of Standard 6 | 0.015625 | mM |
| Standard 8 (blank) | 1000 µl | | 0 | mM |

4. If assaying HRP-PEG$_4$-MAL, add 160 µl of sample to 160 µA of Standard 1 and incubate for 30 minutes. This mixture serves as the unknown for HRP-PEG$_4$-MAL samples. Add 100 µl of this unknown to the appropriate well as described in Step 5.
5. Add 100 µl of each standard or unknown to the appropriate wells of a microtiter plate (attach template).
6. Prepare Ellman's Reagent Solution.
   Ellman's Reagent Solution: Dissolve 8 mg Ellman's in 2 ml Reaction Buffer.
7. Add 20 µl of Ellman's Reagent Solution to each well containing standard or unknown.
8. Mix and incubate at room temperature for 15 minutes.
9. Measure absorbance at 412 nm using the Plate reader.
10. If only raw data available, plot the values obtained for the standards to generate a standard curve.

Analysis:
Experimental concentrations (mM thiol) are determined from the standard curve, where the standard curve gives an equation: Y=mX+b, wherein Y=OD$_{412\ nm}$, X=mM thiol, m=slope (obtained from standard curve equation), and b=x axis intercept (obtain from standard curve equation).

For each sample, the protein concentration in mM is determined by dividing the protein concentration in mg/ml (obtained from total protein assay) by the FW of the sample and multiplying by 1000. Then, the number of thiols per antibody molecule is obtained by dividing the mM thiol experimental concentration obtained from above by the protein concentration in mM obtained from the previous step. The number of maleimides per horseradish peroxidase molecule is determined by first subtracting the experimental mM thiol concentration obtained above from 0.5 mM, and then multiplying this difference by 2 and dividing by the protein concentration in mM.

A typical range for thiolation of an antibody is between about 1 and about 10 thiols per antibody molecules, for example, between about 2 and about 6 such as between about 2 and about 4. A typical range for the number of maleimide groups incorporated per HRP molecule is between about 1 and about 10, for example, between about 3 and about 8 such as between about 5 and about 7.

Determination of the Number of HRPs Per Antibody

Constants
HRP Molecular Weight=40,000 Da
Antibody Molecular Weight=150,000 Da
HRP 280 nm Extinction Coefficient of a 1 percent solution (1 mg/mL)=6.52
Antibody 280 nm Extinction Coefficient of a 1 percent solution (1 mg/mL)=14
HRP Absorbance at 403 nm/Absorbance at 280 nm=2.90 (This value is measured for each different lot of HRP)

Calculations
1) Determine the 280 nm absorbance contribution to the conjugate due to HRP by measuring the conjugate absorbance at 403 nm and applying the equation: HRP Absorbance at 403 nm/2.90=HRP Absorbance at 280 nm.
2) From the value obtained in 1, determine the amount of HRP in mg/ml by applying the equation: HRP Absorbance at 280 nm/6.52=[HRP] in mg/ml.
3) Determine the number of mM HRP by dividing the protein concentration in mg/ml (obtained from 2) by the FW (40,000) and multiplying by 1000.
4) Determine the 280 nm absorbance contribution to the conjugate due to secondary antibody by measuring the conjugate absorbance at 280 nm and subtracting the contribution due to HRP determined in 1.
5) From the value obtained in 4, determine the amount of HRP in mg/ml by applying the equation: Antibody Absorbance at 280 nm/14=[Antibody] in mg/ml
6) Determine the number of mM antibody by dividing the antibody concentration in mg/ml (obtained from 5) by the FW (150,000) and multiplying by 1000.
7) Calculate the number of HRPs per secondary antibody by dividing the mMoles of HRP (determined in 3) by the number of mMoles of secondary antibody (determined in 6)

Determination of the Extinction Coefficient at 280 nm of a One Percent Solution of HRP-Antibody Conjugate The determination of the extinction coefficient at 280 nm of a one percent (1 mg/mL) solution of HRP-antibody conjugate is determined by ascertaining the conjugate protein concentrations, and then measuring the absorbance at 280 nm. Protein concentrations can be measured according to the Pierce Coomasie assay described above.

E. Stability of Conjugates in Immunohistochemical Analyses

Figure 1B:
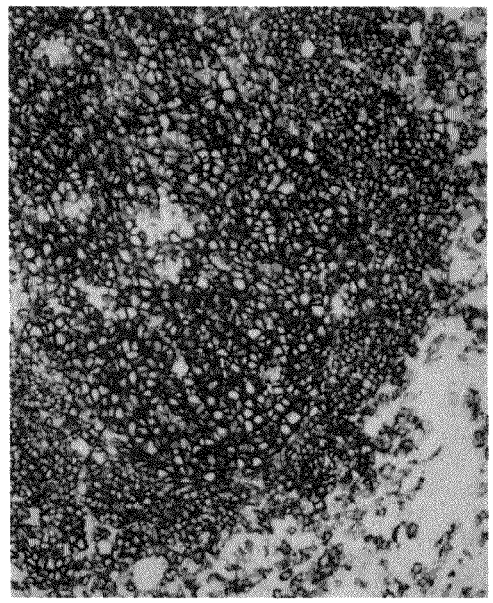
Figure 1C:
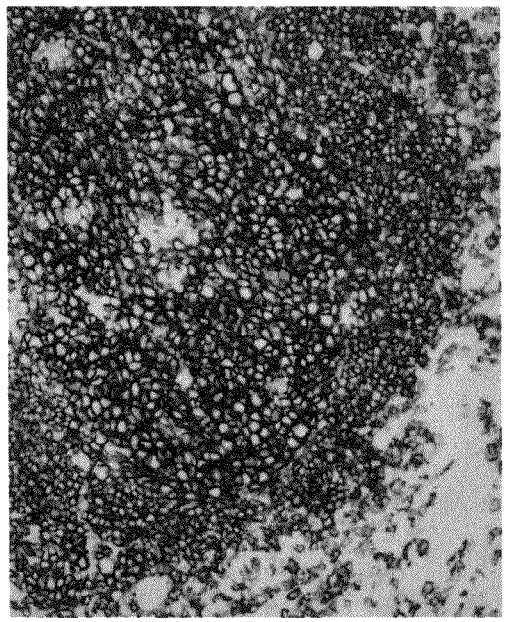
Figure 1D:
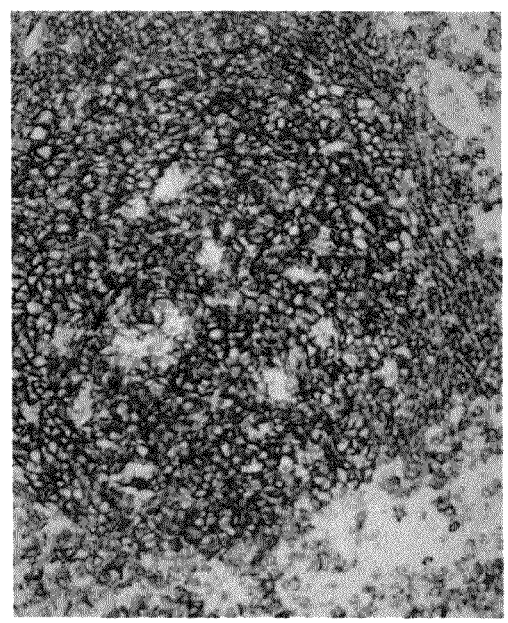

The stability at 45° C. of a cocktail of goat anti-mouse and goat anti-rabbit HRP conjugates in IHC was determined in an Avidin diluent with B5 blocker (Ventana Medical Systems, Inc, Tucson, Ariz.) and the results are shown in FIG. 1A-D. Fixed, paraffin-embedded human tonsil tissue sections were probed using CD20/L26 (mouse) primary antibodies, followed by DAB detection with the cocktail of HRP conjugates according to a standard automated protocol on a Bench-Mark® XT autostainer (Ventana Medical Systems, Inc, Tucson, Ariz.). All slides were done in were done in triplicate. FIG. 1A shows typical results on Day 0 of the test; FIG. 1B shows typical results on Day 1 of the test; FIG. 1C shows typical results on Day 3 of the test; and FIG. 1D shows typical results on Day 7 of the test. Even at the high temperature of 45° C., the disclosed conjugates were not completely degraded (30-40% loss of staining intensity) by day 7, demonstrating that the disclosed conjugates are highly stable.

Similar studies over a longer period were performed for storage at 2-8° C., at 27° C., and at 37° C. (no data shown), and further demonstrated the superior stability of the disclosed conjugates. In summary, at 2-8° C. no change in staining intensity was observed between Day 0 and Week 2. At 27° C. virtually no change in staining intensity was observed between Day 0 and Week 2 for CD20. At 37° C. a ~25% loss in staining intensity was observed over a one week period, and a 30-50% loss in staining intensity was observed after 2 weeks for both CD20 and PSA. At Week 2 there is a 30-50% loss in staining intensity for both CD20 and PSA.

F. IHC Performance Assessment of Conjugates as Secondary Antibodies to Different Primary Antibodies Goat anti-mouse IgG conjugate made with MAL-PEG$_4$-NHS linker, goat anti-rabbit IgG conjugate also made with the same linker, or a mixture of rabbit anti-mouse IgG and the two conjugates ("amplification") was used as a secondary antibody reagent for detection of binding to tissue antigens of the primary antibodies that are listed below (available from Ventana Medical Systems, Inc, Tucson, Ariz.). Appropriate archival tissue sections were treated with these conjugates and developed using standard protocols for HRP signal generation (by addition of DAB) on an automated stainer (BenchMark® XT, Ventana Medical Systems, Inc, Tucson, Ariz.). A typical automated protocol includes deparaffinization, several rinse steps, addition of a reaction buffer, addition of the primary antibody, addition of the secondary antibody, addition of DAB and hydrogen peroxide, and addition of a counterstain.

Comparable (adjacent) tissue sections were stained with the disclosed conjugates and with polylysine-scaffolded HRP/F(ab')$_2$ conjugates (hereinafter "scaffolded conjugates") used as the secondary antibody reagent. The scaffolded conjugates were either a second generation scaffolded conjugate (smaller, more homogeneous as determined by size-exclusion chromatography) or a first generation (larger, more inhomogeneous as determined by size-exclusion chromatography). See, U.S. Pat. Nos. 6,613,564 and 6,252,053 for a more complete description of the scaffolded conjugates.

Antibodies

| | |
|---|---|
| Anti-bcl-2 (clone 100/D5) | Anti-CD57 (clone NK-1) |
| Anti-CD15 (clone MMA) | Anti-CD23 (clone 1B12) |
| Anti-CD20 (clone L26) | Anti-ER(clone 6F11) |
| Anti-PR (clone 16) | Anti-p53 (clone D07) |
| Anti-EGFR (clone 31G7) | Anti-Cyclin-d1 (clone P2D11F11) |
| Anti-c-erbB-2 (clone CB11) | Anti-PSA |

*note: all were mouse antibodies, with the exception of PSA, which is a rabbit antibody.

Figure 2A:
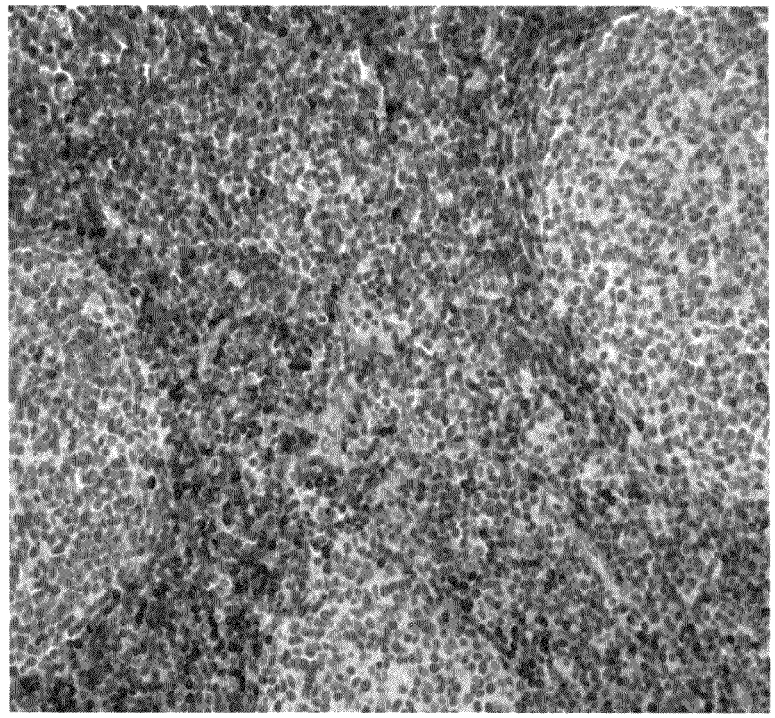
FIGS. 2A-2B are images comparing the staining intensity of a disclosed conjugate and a scaffolded conjugate for immunohistochemical staining of bcl-2.
Figure 2B:
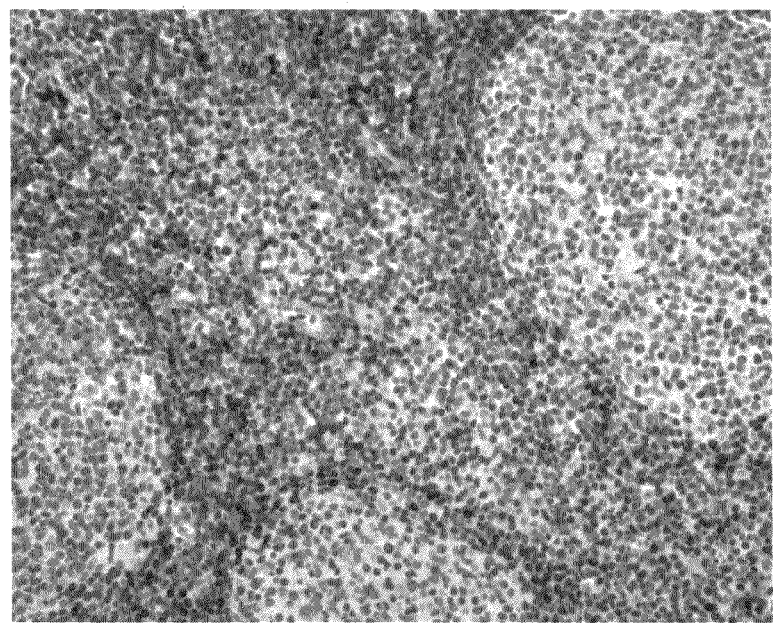

FIG. 2 shows the staining results for bcl-2 detection for the disclosed conjugate (FIG. 2A) and the second generation scaffolded conjugate (FIG. 2B). The results demonstrate that higher intensity staining is achieved with the disclosed conjugate in comparable tissue sections.

Figure 3A:
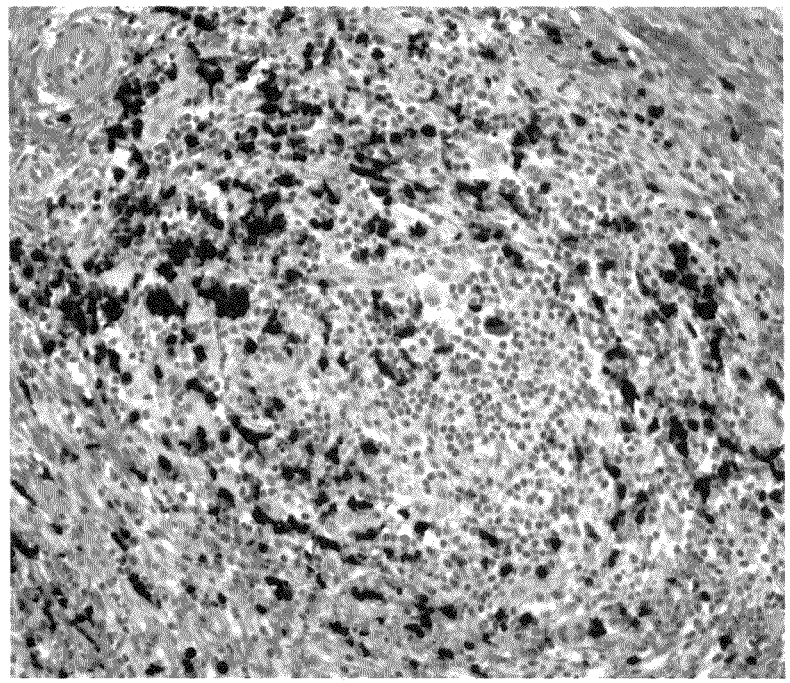
FIGS. 3A-3B are images comparing the staining intensity of a disclosed conjugate and a scaffolded conjugate for immunohistochemical staining of CD15.
Figure 3B:
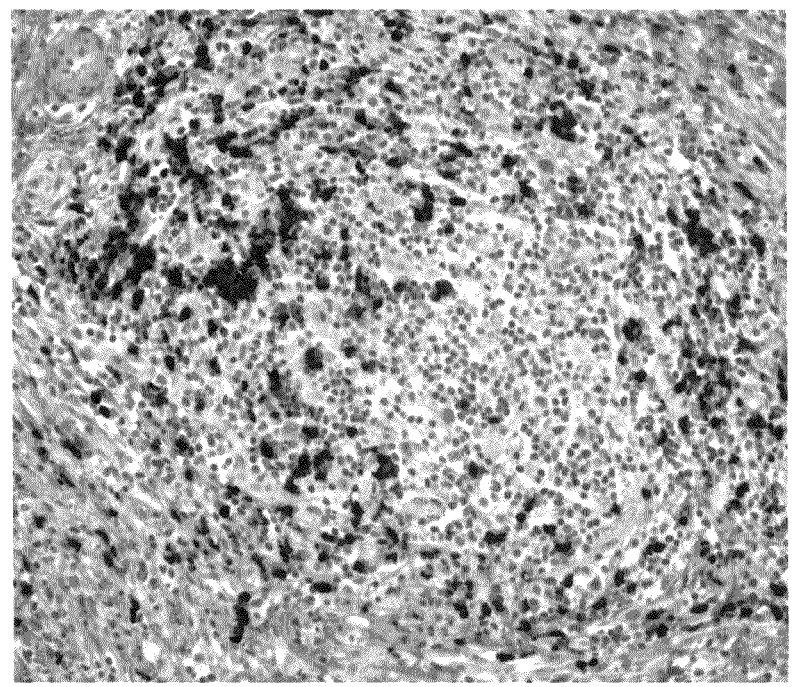

FIG. 3 shows the staining results for CD-15 detection using the disclosed conjugate (FIG. 3A) and the second generation scaffolded conjugate (FIG. 3B). The results demonstrate higher intensity staining is achieved with the disclosed conjugate in comparable tissue sections.

Figure 4A:
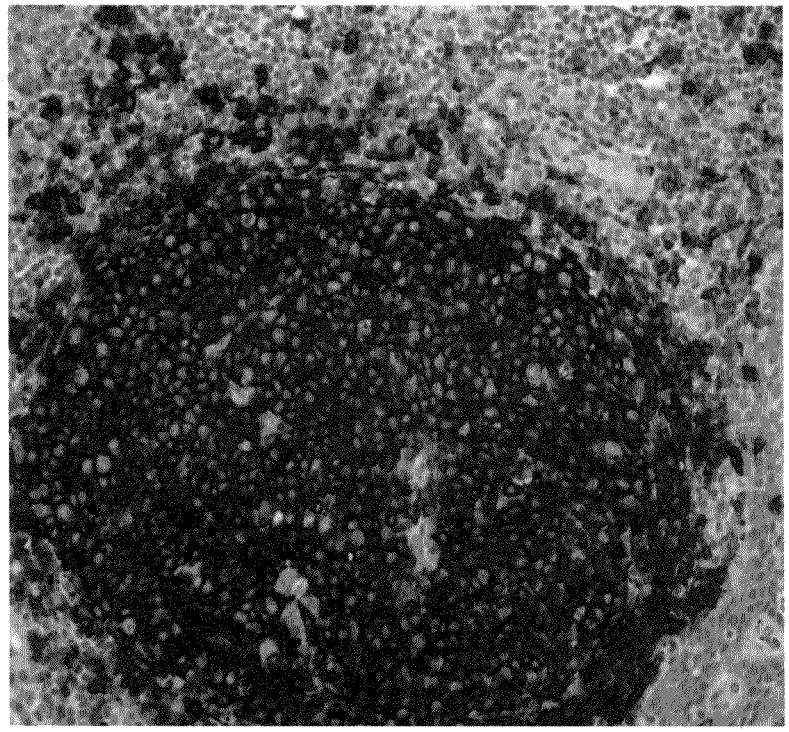
FIGS. 4A-4B are images comparing the staining intensity of a disclosed conjugate and a scaffolded conjugate for immunohistochemical staining of CD20.
Figure 4B:
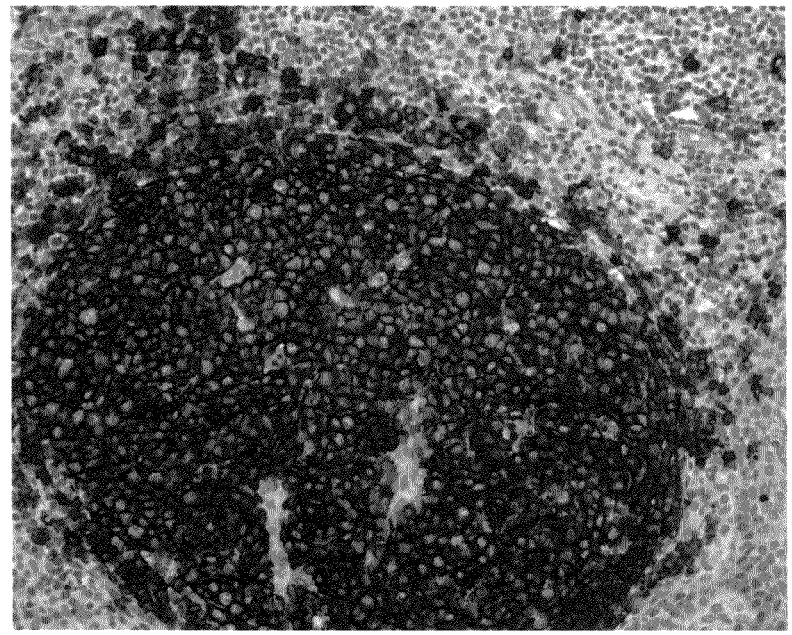

FIG. 4 shows the staining results for CD-20 detection using the disclosed conjugate (amplification utilized, FIG. 4A) and the second generation scaffolded conjugate (FIG. 4B). The results demonstrate higher intensity staining is achieved with the disclosed conjugate in comparable tissue sections.

Figure 5A:
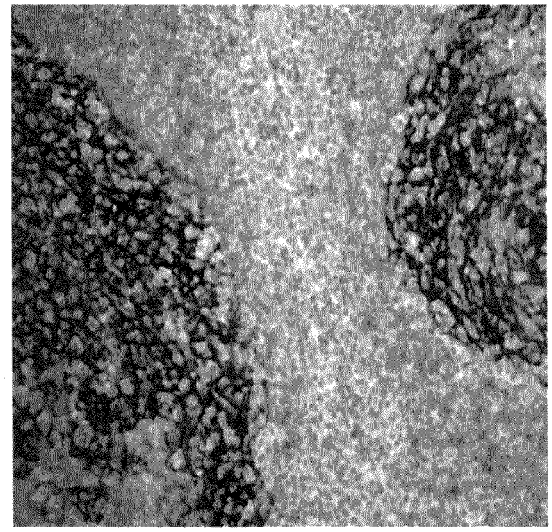
FIGS. 5A-5C are images comparing the staining intensity of a disclosed conjugate and two scaffolded conjugates for immunohistochemical staining of CD23.
Figure 5B:
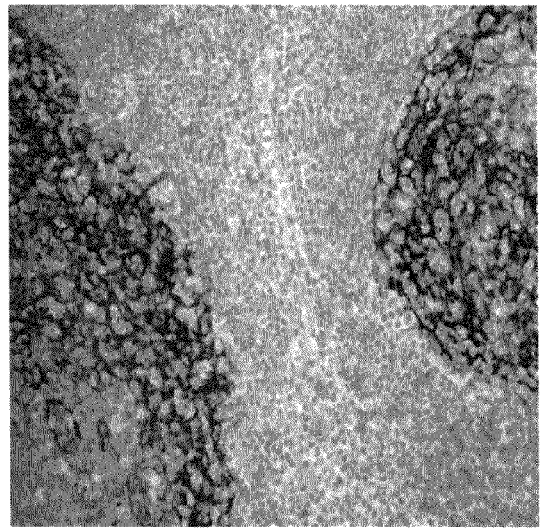
Figure 5C:
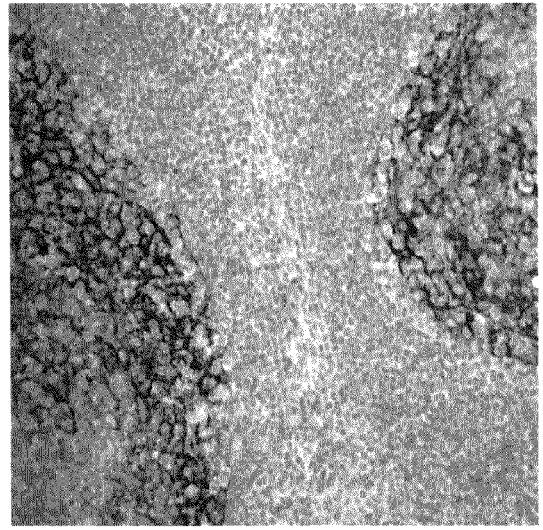

FIG. 5 shows the staining results for CD-23 detection using the disclosed conjugate (FIG. 5A), the second generation scaffolded conjugate (FIG. 5B), and the first generation scaffolded conjugate (FIG. 5C). The results demonstrate higher intensity staining is achieved with the disclosed conjugate in comparable tissue sections than is seen for both scaffolded conjugates.

Figure 6A:
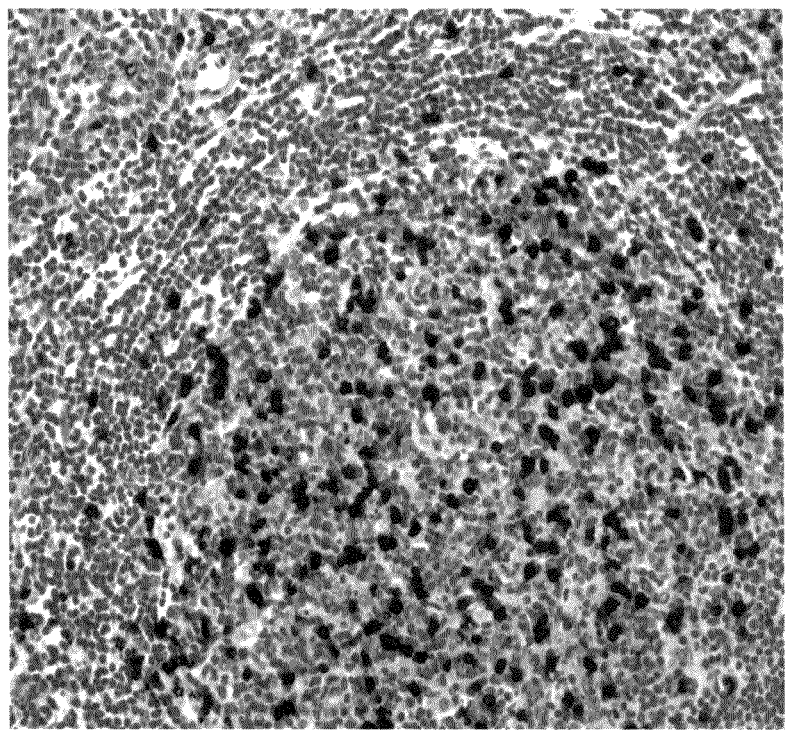
FIGS. 6A-6B are images comparing the staining intensity of a disclosed conjugate and a scaffolded conjugate for immunohistochemical staining of CD57.
Figure 6B:
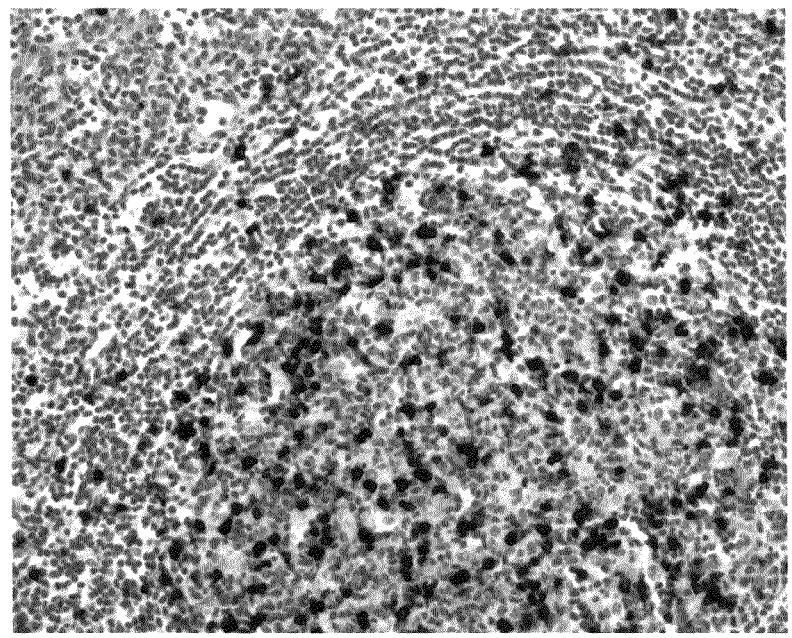

FIG. 6 shows the staining results for CD57 detection using the disclosed conjugate (FIG. 6A) and the second generation scaffolded conjugate (FIG. 6B). The results demonstrate higher intensity staining is achieved with the disclosed conjugate in comparable tissue sections.

Figure 7A:
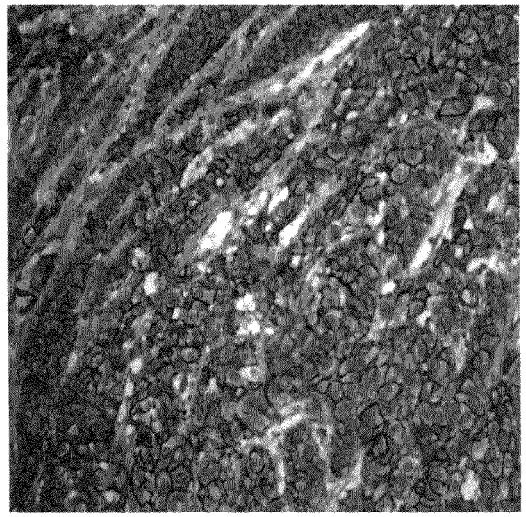
FIGS. 7A-7C are images comparing the staining intensity of a disclosed conjugate and two scaffolded conjugates for immunohistochemical staining of cerbB2.
Figure 7B:
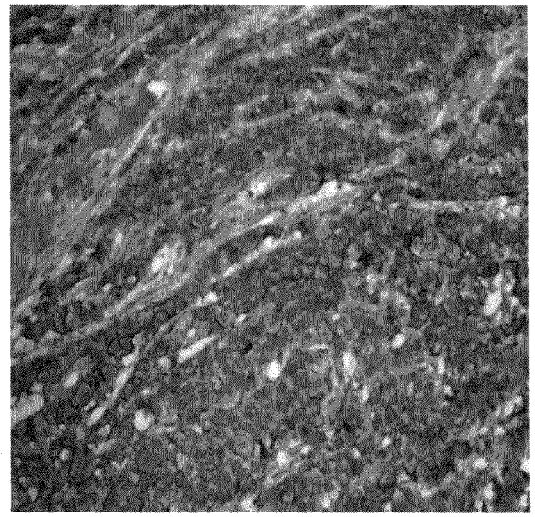
Figure 7C:
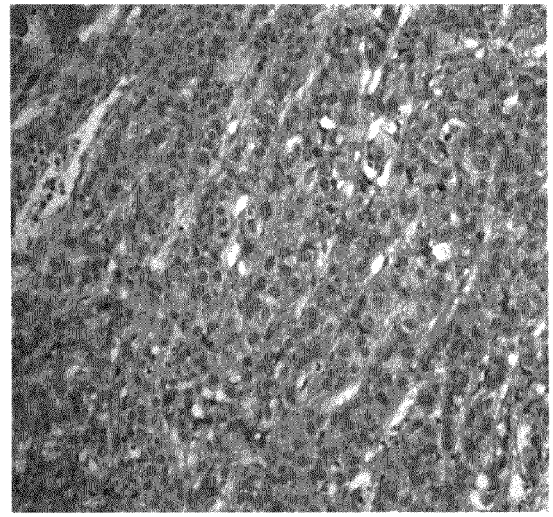

FIG. 7 shows the staining results for cerb-B2/CB11 detection using the disclosed conjugate (FIG. 7A), the second generation scaffolded conjugate (FIG. 7B), and the first generation scaffolded conjugate (FIG. 7C). The results demonstrate higher intensity staining is achieved with the disclosed conjugate in comparable tissue sections than is seen for both scaffolded conjugates.

Figure 8A:
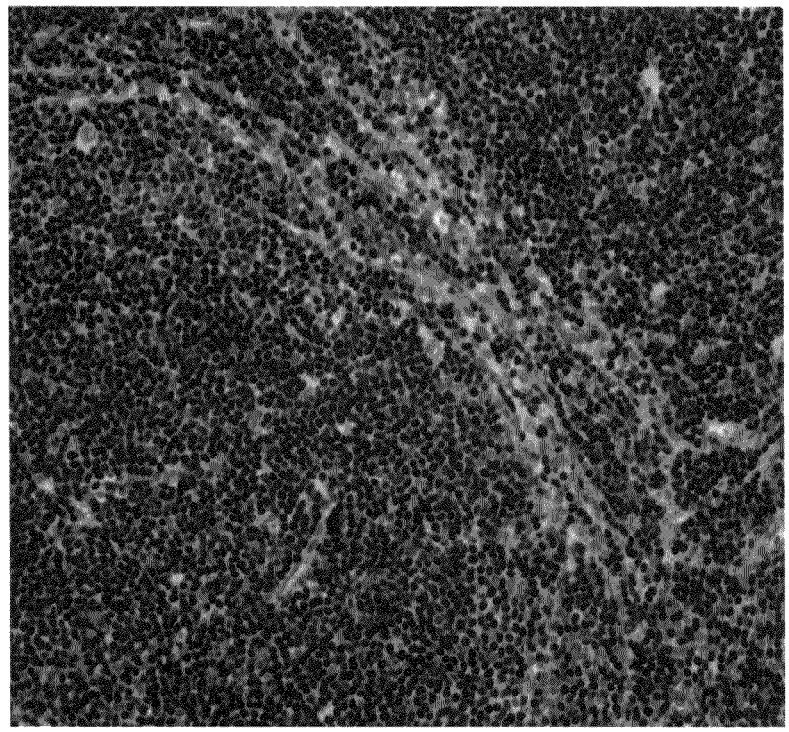
FIGS. 8A-8B are images comparing the staining intensity of a disclosed conjugate and a scaffolded conjugate for immunohistochemical staining of cyclin D1.
Figure 8B:
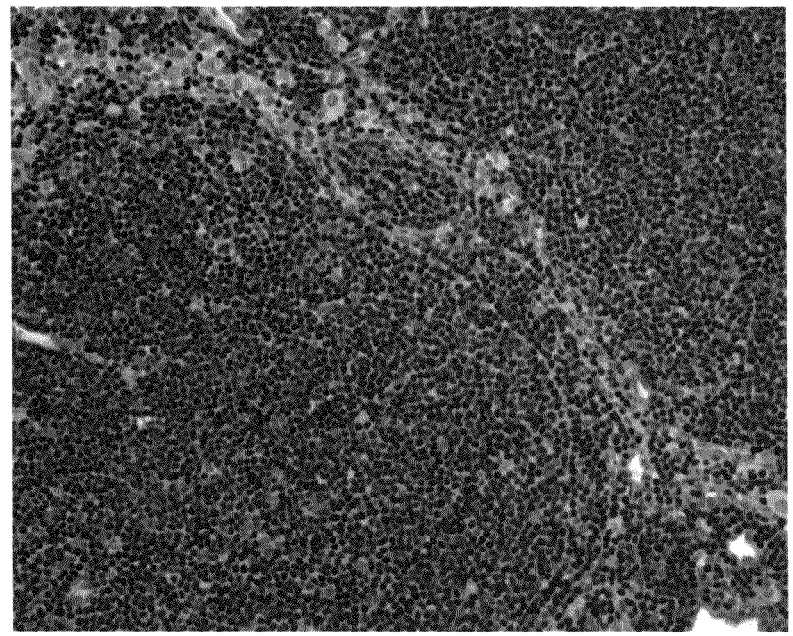

FIG. 8 shows the staining results for cyclin D1 detection using the disclosed conjugate (FIG. 8A) and the second generation scaffolded conjugate (FIG. 8B). The results demonstrate higher intensity staining is achieved with the disclosed conjugate in comparable tissue sections.

Figure 9A:
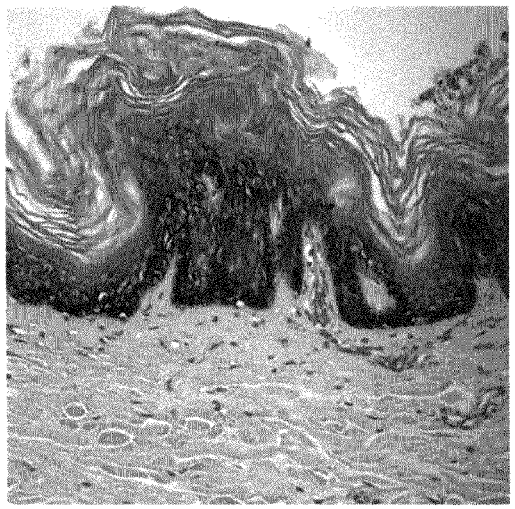
FIGS. 9A-9C are images comparing the staining intensity of a disclosed conjugate and two scaffolded conjugates for immunohistochemical staining of EGFR.
Figure 9B:
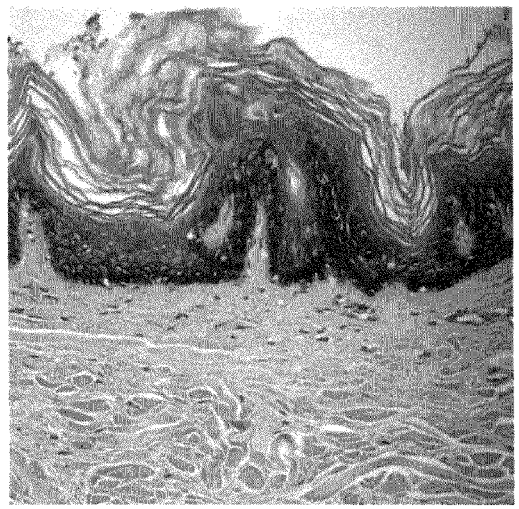
Figure 9C:
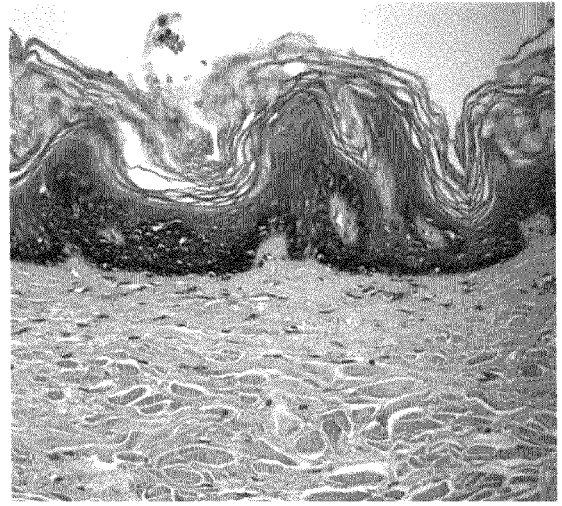

FIG. 9 shows the staining results for EGFR detection using the disclosed conjugate (FIG. 9A), the second generation scaffolded conjugate (FIG. 9B), and the first generation scaffolded conjugate (FIG. 9C). The results demonstrate higher intensity staining is achieved with the disclosed conjugate in comparable tissue sections than is seen for both scaffolded conjugates.

Figure 10A:
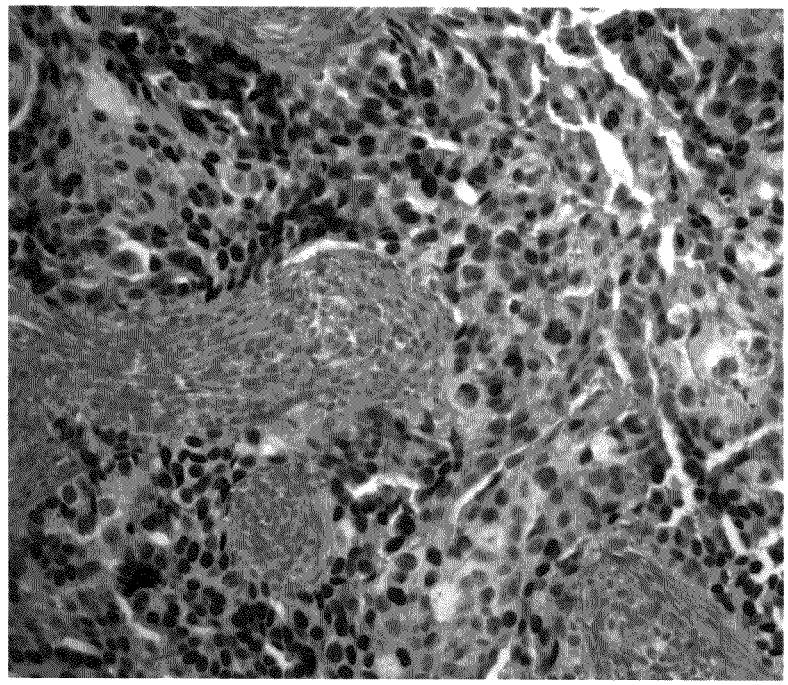
FIGS. 10A-10B are images comparing the staining intensity of a disclosed conjugate and a scaffolded conjugate for immunohistochemical staining of ER.
Figure 10B:
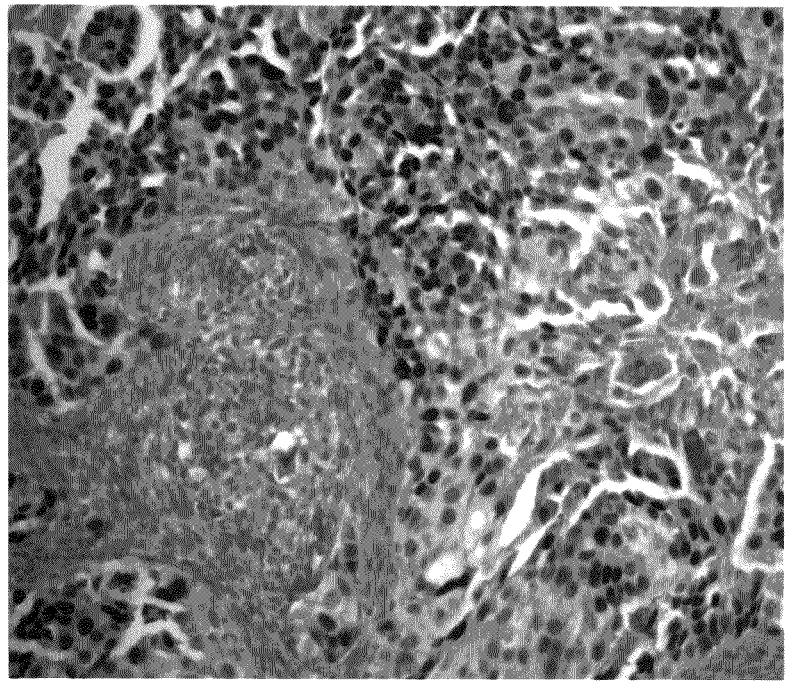

FIG. 10 shows the staining results for ER detection using the disclosed conjugate (FIG. 10A) and the second generation scaffolded conjugate (FIG. 10B). The results demonstrate higher intensity staining is achieved with the disclosed conjugate in comparable tissue sections.

Figure 11A:
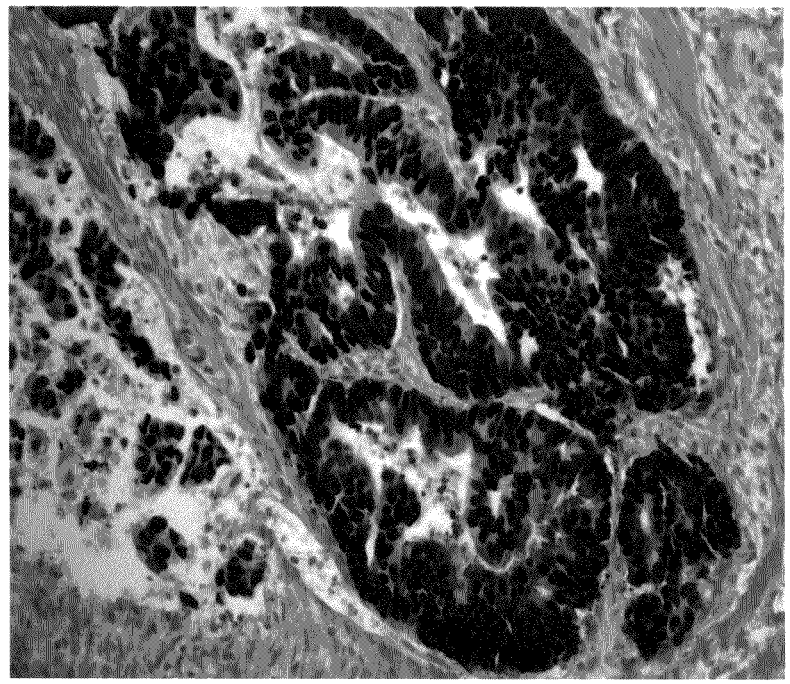
FIGS. 11A-11B are images comparing the staining intensity of a disclosed conjugate and a scaffolded conjugate for immunohistochemical staining of p53.
Figure 11B:
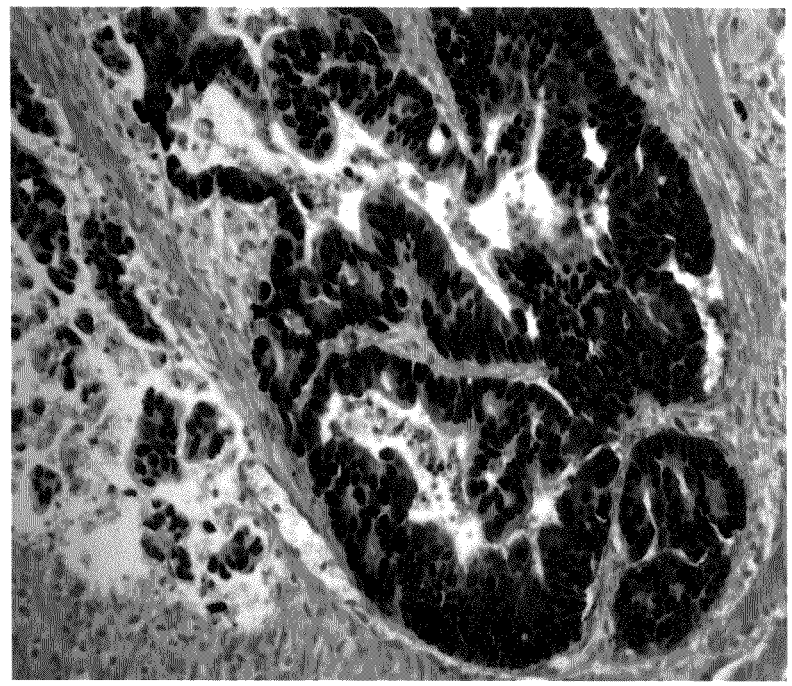

FIG. 11 shows the staining results for p53 detection using the disclosed conjugate (FIG. 11A) and the second generation scaffolded conjugate (FIG. 11B). The results demonstrate comparable staining is achieved between the disclosed conjugate and the scaffolded conjugate in comparable tissue sections.

Figure 12A:
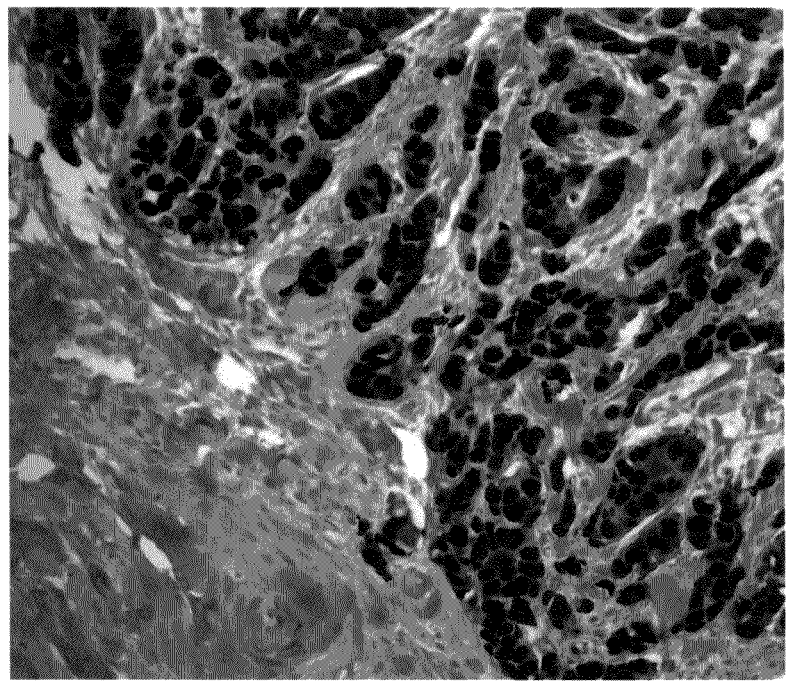
FIGS. 12A-12B are images comparing the staining intensity of a disclosed conjugate and a scaffolded conjugate for immunohistochemical staining of PR.
Figure 12B:
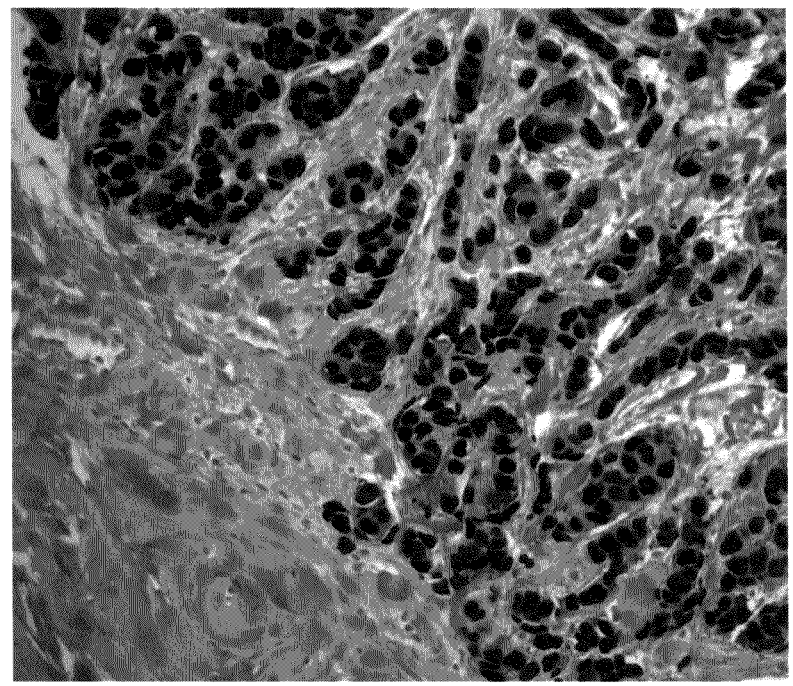

FIG. 12 shows the staining results for PR detection using the disclosed conjugate (FIG. 12A) and the second generation scaffolded conjugate (FIG. 12B). The results demonstrate higher intensity staining is achieved with the disclosed conjugate in comparable tissue sections.

Figure 13A:
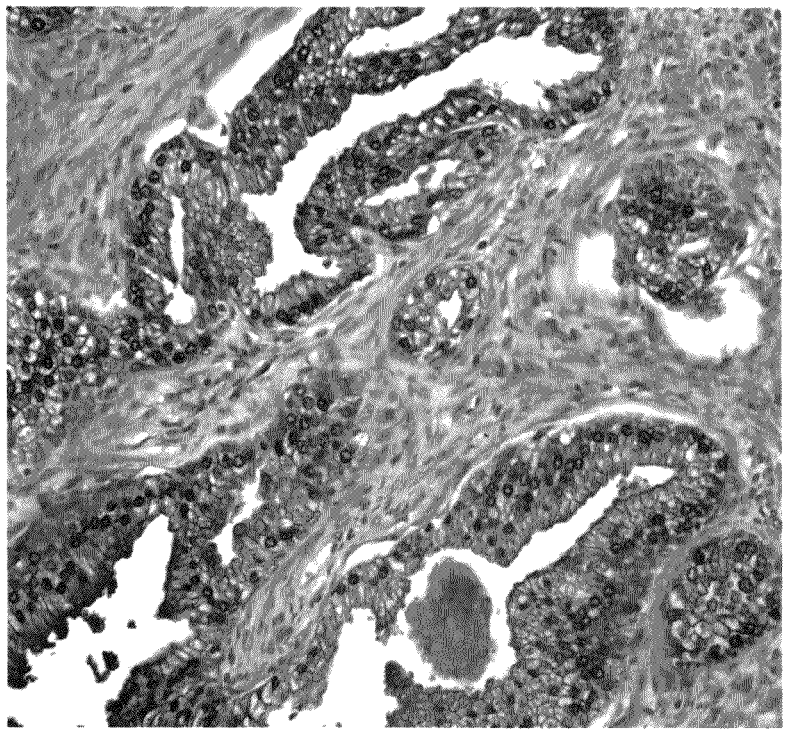
FIGS. 13A-13B are images comparing the staining intensity of a disclosed conjugate and a scaffolded conjugate for immunohistochemical staining of PSA.
Figure 13B:
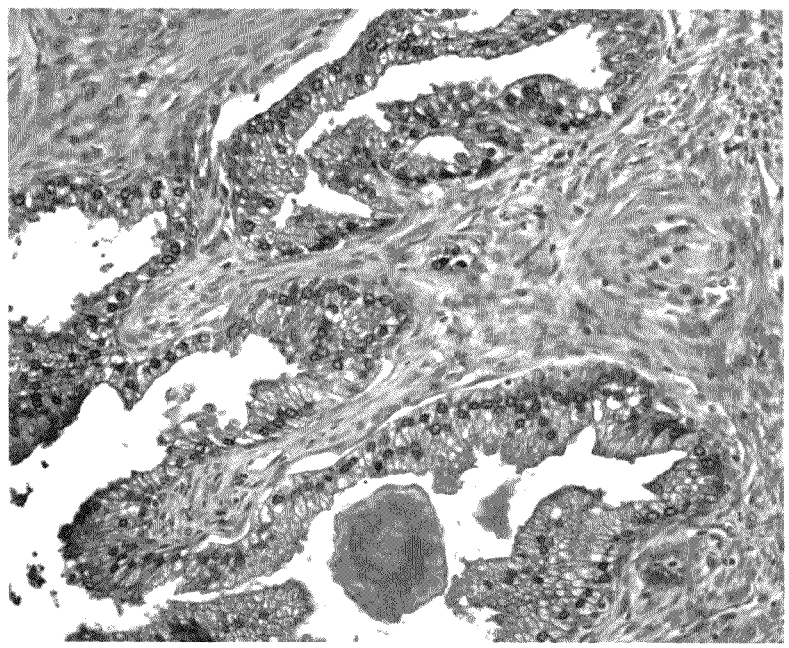

FIG. 13 shows the staining results for PSA detection using the disclosed conjugate (FIG. 13A) and the second generation scaffolded conjugate (FIG. 13B). The results demonstrate higher intensity staining is achieved with the disclosed conjugate in comparable tissue sections.

In conclusion, the results of tissue testing of the disclosed conjugate detection compositions demonstrated that the disclosed conjugates perform significantly better for tissue staining than scaffolded conjugates.

G. Stability of Conjugates at 37° C. and 45° C. for Enzyme Metallographic Detection of Nucleic Acid Sequences.

Figure 14:
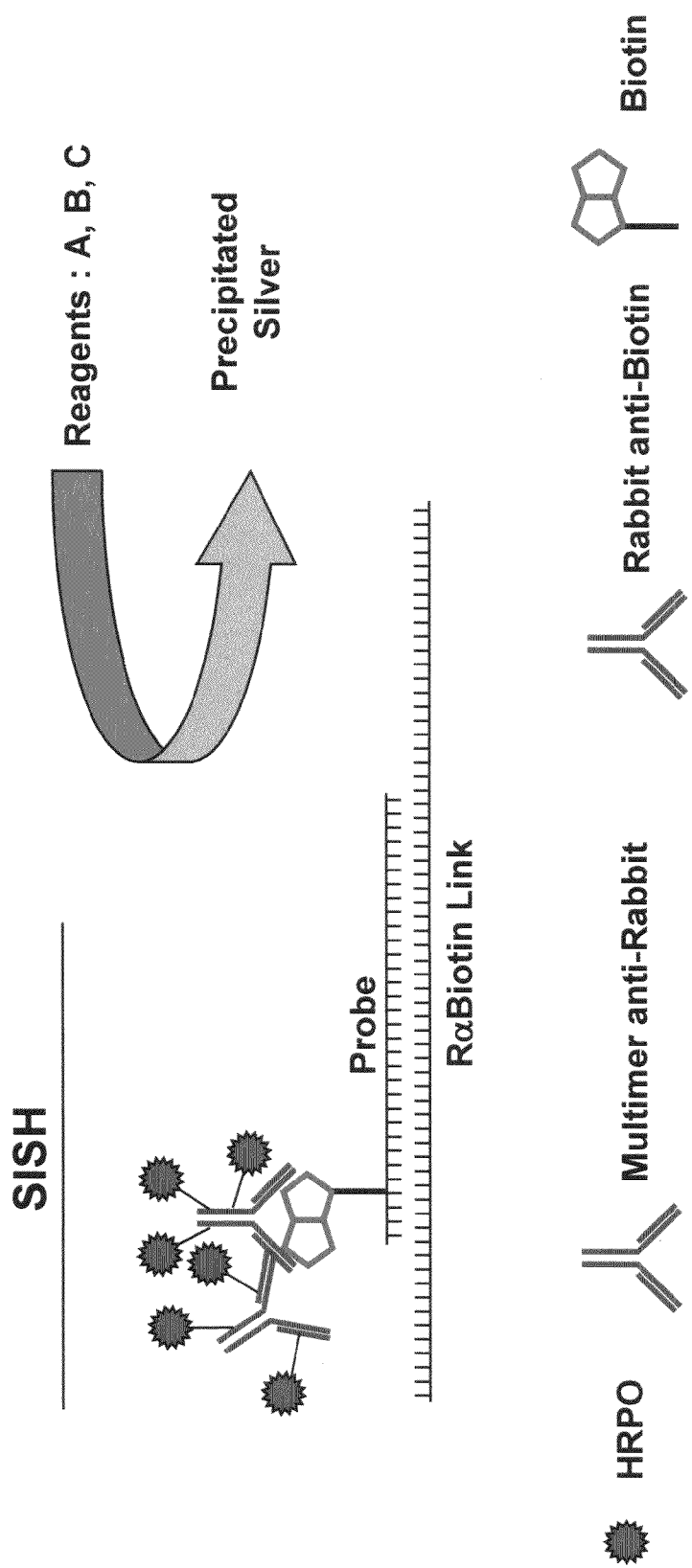
FIG. 14 is a diagram outlining a scheme for enzyme metallographic detection of binding of a hapten-labeled nucleic acid probe to a target nucleic acid sequence that utilizes a disclosed antibody-enzyme conjugate.

Experiments were performed to assess the stability over time of a goat anti-rabbit IgG antibody-HRP (PEG4) conjugate at 45° C. and at 37° C. In this instance, stability of the conjugates was assessed in an assay involving enzyme metallographic detection (EnzMet, Nanoprobes Inc., Yaphank, N.Y.) of nucleic acid sequences. As illustrated in FIG. 14, biotin-labeled probe DNA was detected with a combination of an anti-biotin rabbit conjugate and anti-rabbit IgG conjugate. The conjugate mixture was stored in Stabilzyme Select (Surmodics, Eden Prairie, Minn.) as the diluent. The stability of the second generation scaffolded conjugate discussed in Example D above, was also examined over the same time period.

Figure 15A:
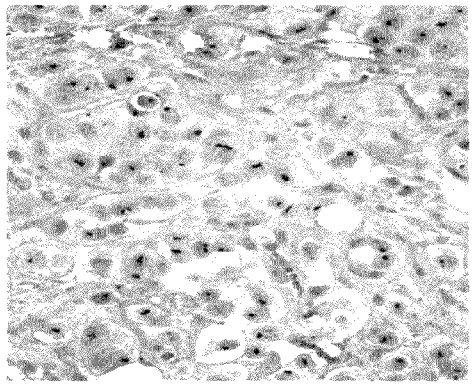
FIGS. 15A-15F are images of tissue sections treated for enzyme metallographic ISH detection of a nucleic acid sequence using a disclosed conjugate and a scaffolded conjugate, before and after storage both at 37° C. for 7 days and at 45° C. for 7 days.
Figure 15B:
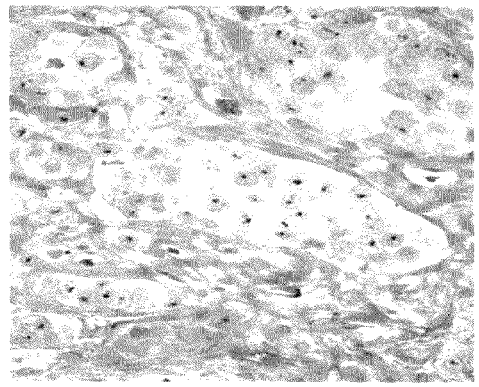
Figure 15C:
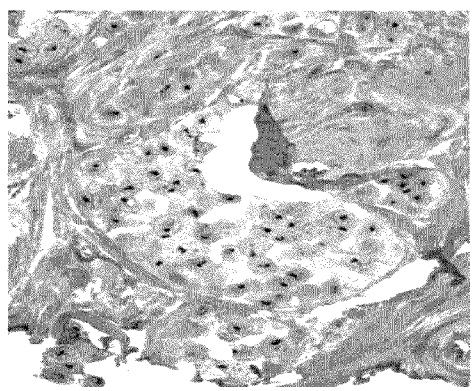
Figure 15D:
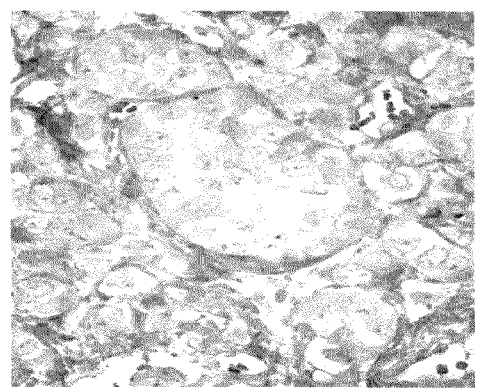
Figure 15E:
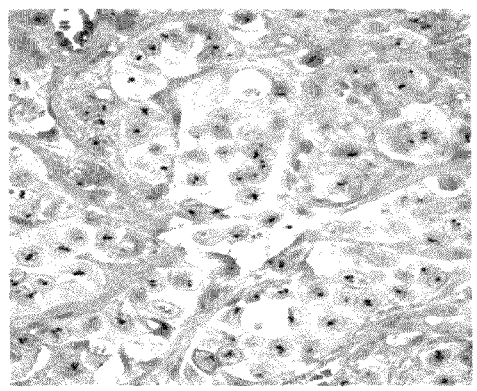
Figure 15F:
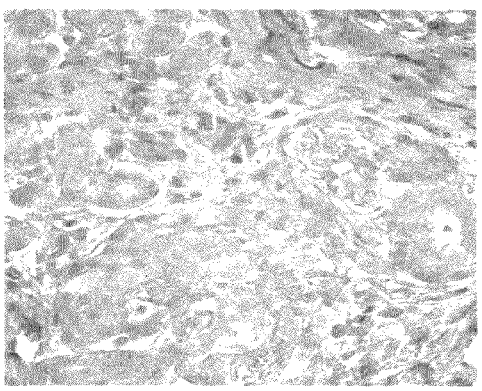

FIG. 15A shows a tissue stained with the disclosed conjugate at day 0, which may be compared to the tissue stained with the scaffolded conjugate at day 0 in FIG. 15B. FIG. 15C shows a tissue stained with the disclosed conjugate at day 7 after storage at 37° C. for 7 days, which may be compared to the tissue stained with the scaffolded conjugate at day 7 after storage at 37° C. for 7 days in FIG. 15D. FIG. 15E shows a tissue stained with the disclosed conjugate at day 7 after storage at 45° C. for 7 days, which may be compared to the tissue stained with the scaffolded conjugate at day 7 after storage at 45° C. for 7 days in FIG. 15F. The tissue staining intensity shown in the figures demonstrates the superior stability of the disclosed conjugate at both temperatures over a period of 7 days, with the scaffolded conjugate showing complete loss of staining ability after 7 days at the higher temperature.

Figure 16A:
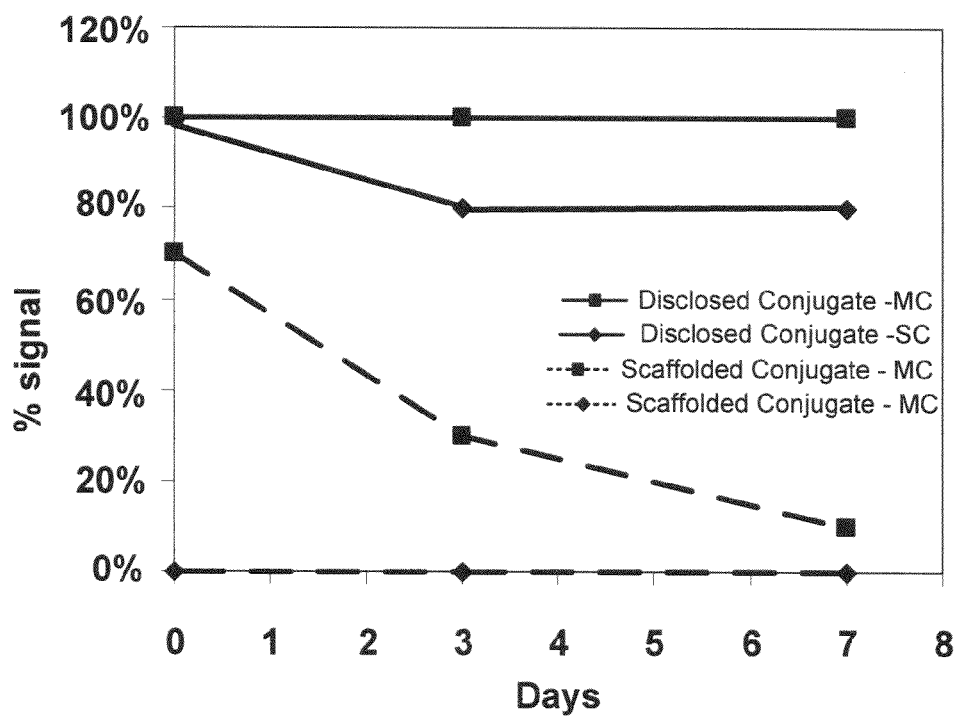
FIGS. 16A-16B are graphs comparing the stability of a disclosed conjugate and a scaffolded conjugate in an enzyme metallographic detection scheme.
Figure 16B:
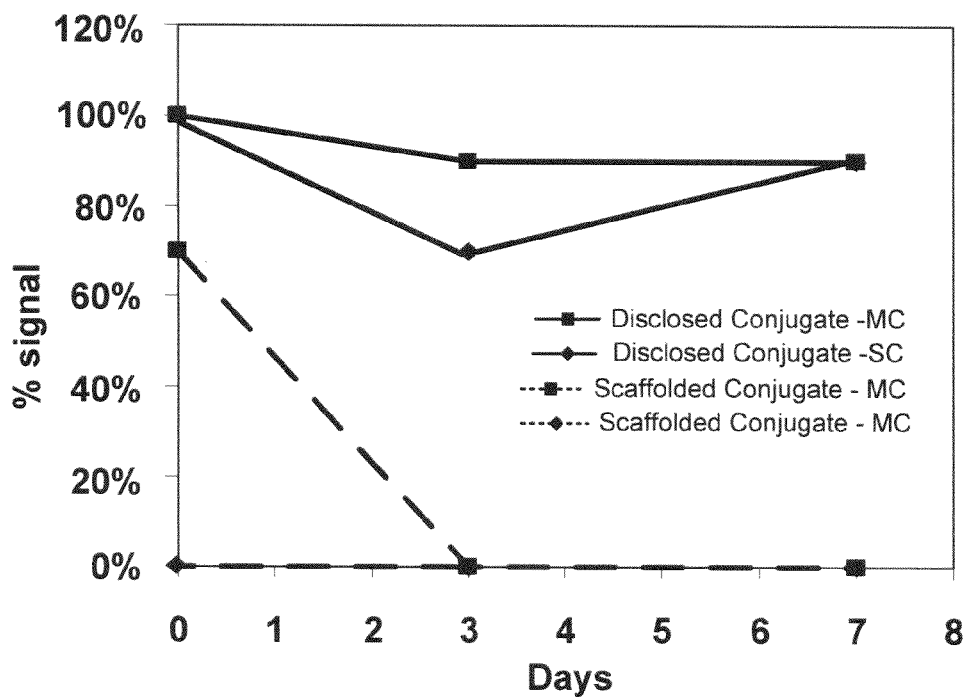

The relative stability over time of the disclosed conjugate and the scaffolded conjugate for detecting single copy and for detecting multiple copies of a target DNA sequence is shown in graphic form in FIG. 16A (37° C.) and FIG. 16B (45° C.). The graphs illustrate how much less effective the scaffolded conjugate is for enzyme metallography of both single and multiple copy targets, how the scaffolded conjugate is completely ineffective for single copy detection while the disclosed conjugate was effective for single copy detection even after many days of storage at elevated temperature, and how the disclosed conjugate maintains its ability for multiple copy detection over time at both temperatures while the scaffolded conjugate quickly loses its ability to amplify the gene signal at both temperatures.

H. Effect of Reaction Conditions on Conjugate Composition

The reproducibility with which a well defined antibody-HRP conjugate could be made was investigated by looking at the effect of DTT reduction time of the antibody, length of the linker as well as type, stoichiometry of linker added, HRP concentration in the coupling reaction, and the molar ratio of HRP to antibody. Size exclusion chromatography on an AKTA Purifier LC fitted with a Superdex 10/300,200 GL column (Amersham, Piscataway, N.J.) was used make initial comparisons. The mobile phase used was phosphate buffered saline, pH=7.5 with a flow rate of 1 ml/min.

Variation of DTT Reduction Time

Figure 17:
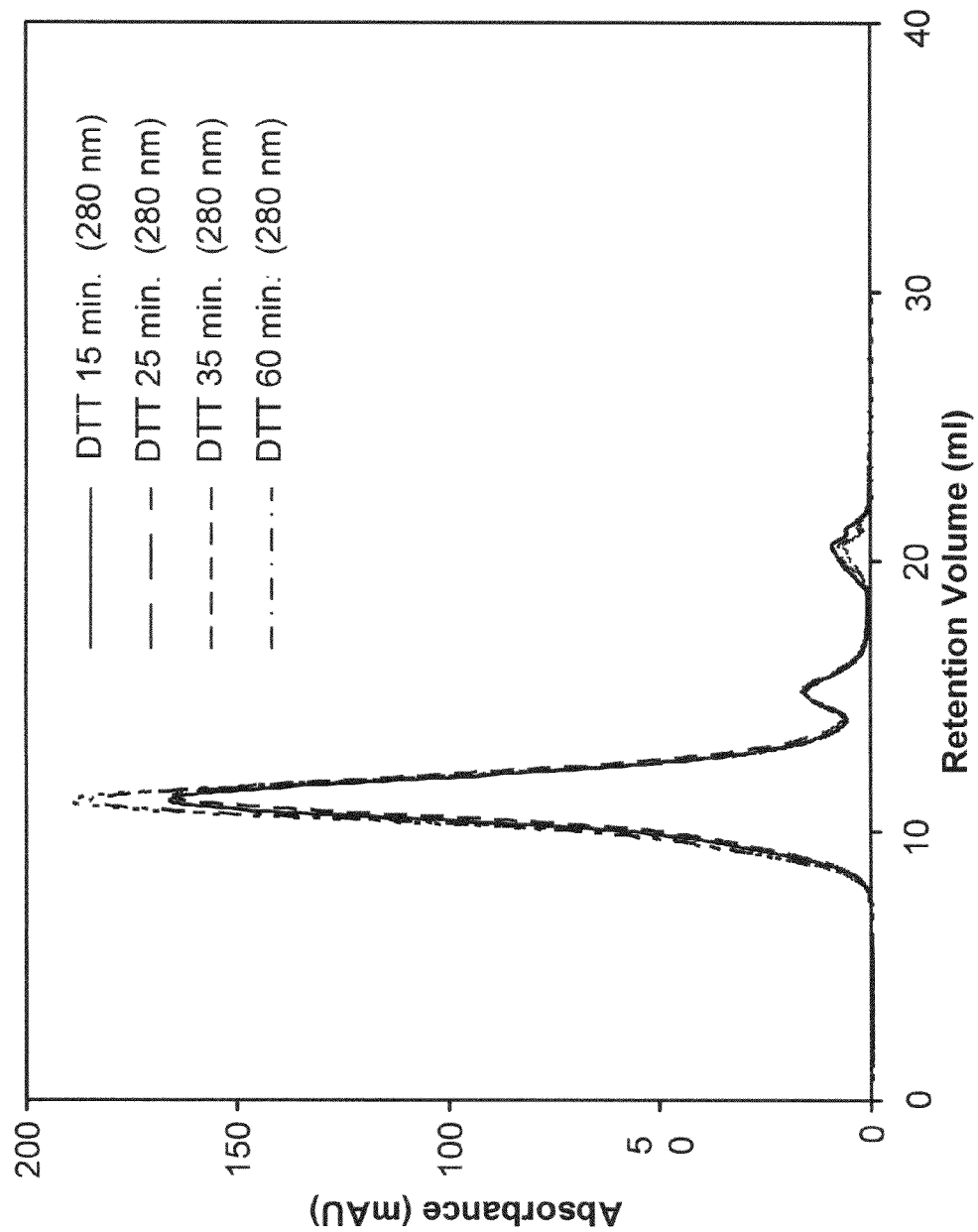
FIG. 17 is a size-exclusion chromatogram comparing the effect of variations of antibody reduction time on the MW profile of a disclosed conjugate.

Following the synthetic protocol for the conjugate previously outlined in Example B, a series of reactions were set up in which the incubation time with DTT (25 mM) was varied. The following time points were tested: 15 min, 25 min, 35 min, and 60 min. After performing the coupling reaction between the antibody and maleimide derivatized HRP, the size exclusion chromatograms illustrated in FIG. 17. It was evident that by changing the time period of the DTT treatment that the composition of the conjugate was not significantly altered. The staining obtained with these conjugates on tissue (tonsil, Ki-67) showed no significant change in staining specificity or intensity, with a 15 min DTT treatment being only slightly better than the rest. However, with the other three time points giving identical staining on tissue, this study indicates that the time sensitive nature of the DTT reduction is not overly critical in the production of a reproducible, active conjugate according to the disclosed methods.

Variation of Linker Length/Type

Figure 18:
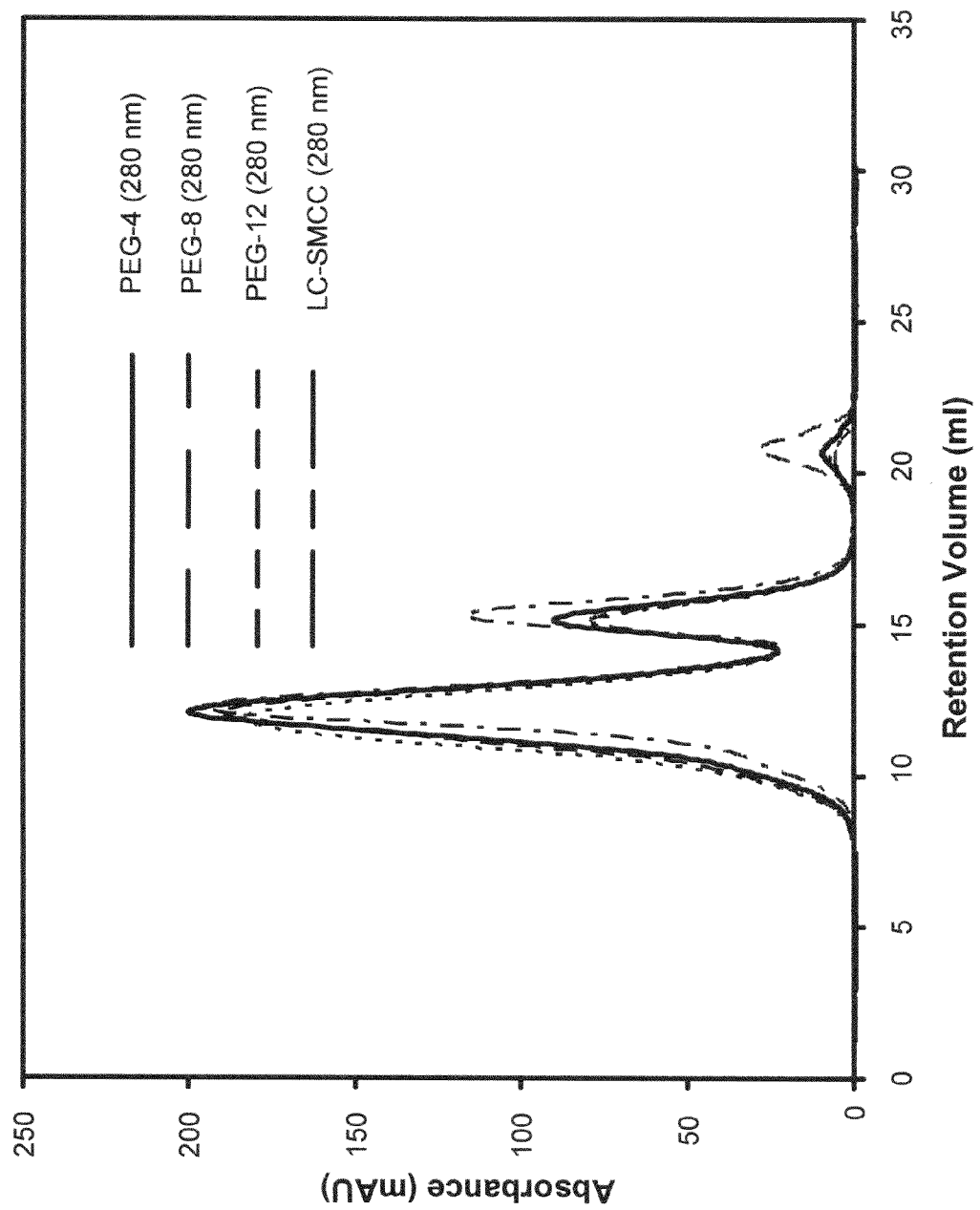
FIG. 18 is a size-exclusion chromatogram comparing the effect of variations of linker size and type on the MW profile of disclosed conjugates.

Following the procedure of Example B, a series of reactions were set up altering the linker type and size. The following linkers were used: LC-SMCC (16 atom hydrophobic linker, Pierce, Rockford Ill.), MAL-dPEG$_8$-NHS ester (34 atom hydrophilic linker, Quanta Biodesign, Inc., Powell Ohio), MAL-dPEG$_{12}$-NHS ester (46 atom hydrophilic linker, Quanta Biodesign, Inc., Powell Ohio), as well as the recommended MAL-dPEG$_4$-NHS ester (22 atom hydrophilic linker, Quanta Biodesign, Inc., Powell Ohio). Each of these linkers was used in a hundred-fold excess, in a buffer (0.1 M sodium phosphate, pH=7.5) for 1 hour. The LC-SMCC was dissolved in dimethylformamide (DMF) and added to the HRP, but not exceeding 10% total volume of DMF in buffer. After coupling to the DTT-treated antibody, size exclusion chromatograms (FIG. 18) were obtained upon purification. Each of the three PEG linkers, based on retention volume, performed comparatively well, the LC-SMCC linker, however, showed less conjugation to the HRP (larger peak at ~16 min) and an overall smaller conjugate.

Figure 19A:
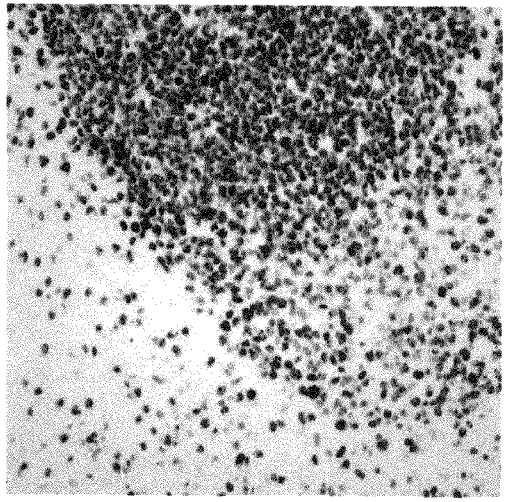
FIGS. 19A-19D are images comparing the staining intensity of several disclosed conjugates compared to a conjugate prepared with an extended-length non-PEG linker.
Figure 19B:
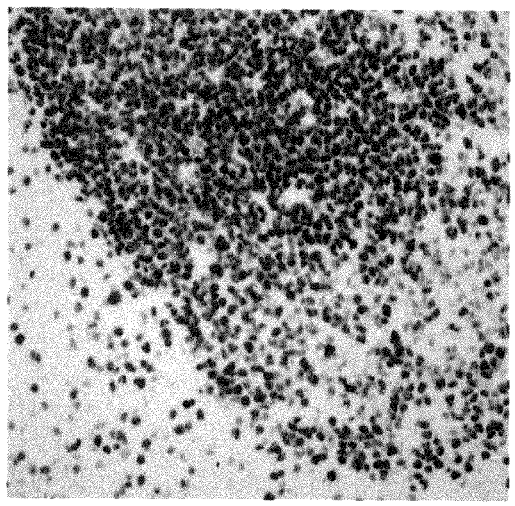
Figure 19C:
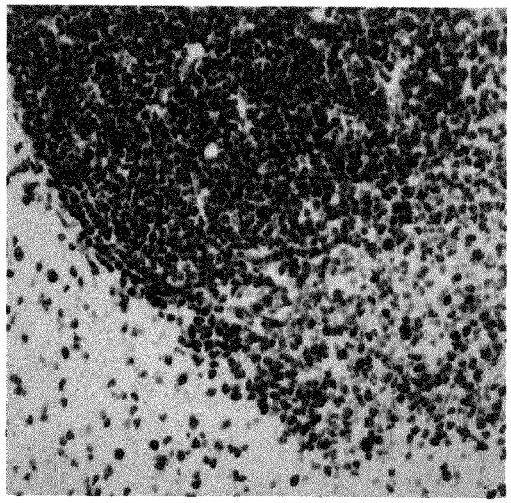
Figure 19D:
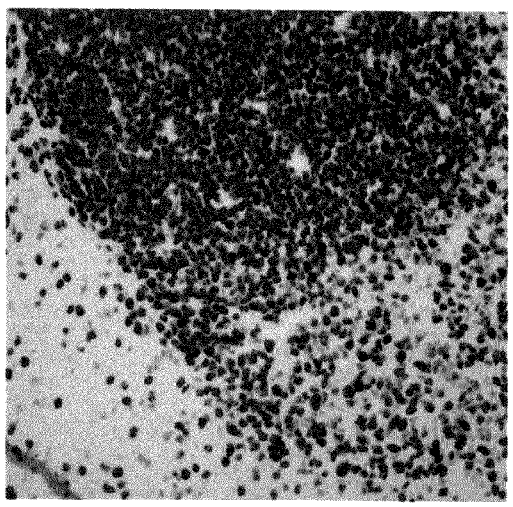

Differences were evident in the immunohistochemical tissue staining intensity (Ki-67 primary antibody/conjugate secondary antibody, with amplification, on tonsil tissue) afforded by the different conjugates (FIG. 19), and the LC-SMCC conjugate gave the lightest amount of staining. Each of the staining runs was done with the conjugates at equivalent 280 nm absorbances ($A_{280}$=0.075), and therefore make the data directly comparable. The three PEG derived conjugates performed surprisingly better than the LC-SMCC (FIG. 19A), and there were differences in the staining intensity afforded by each of them. It is clear from the figures that the PEG$_{12}$ (FIG. 19D) had the darkest overall staining followed by the PEG$_8$ (FIG. 19C) and then PEG$_4$ (FIG. 19D). As will be discussed further below with respect to in situ hybridization assays, the intense staining obtained with conjugates prepared with longer linkers can surprisingly obviate the need for amplification steps during staining.

Variation of Linker Stoichiometry

Figure 20:
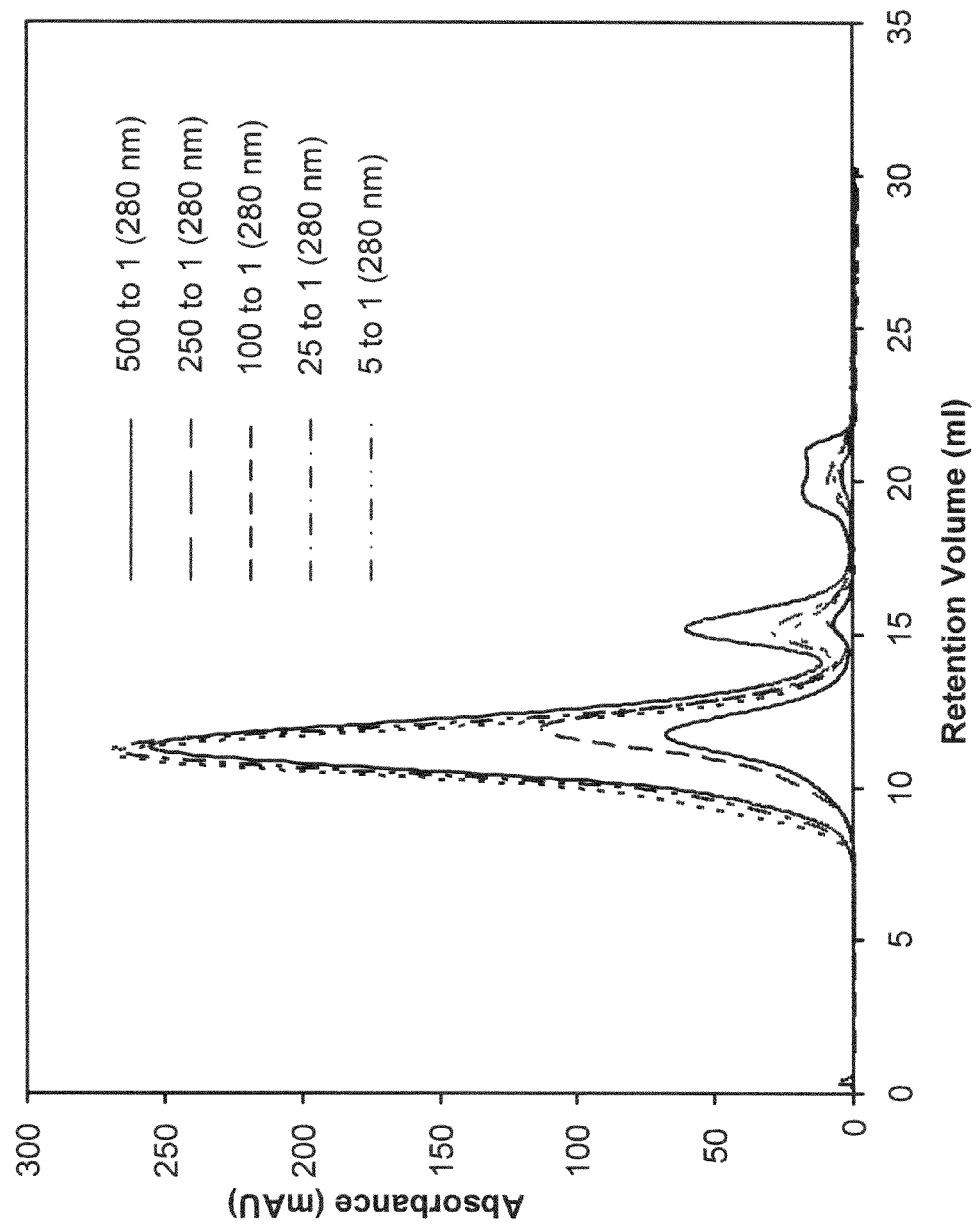
FIG. 20 is a size-exclusion chromatogram comparing the effect of variations of linker excess on the MW profile of a disclosed conjugate.

The synthesis of the HRP-IgG conjugate was carried out following the conjugation procedure of Example B, but the molar excess of MAL-PEG$_4$-NHS ester linker over the HRP amount was varied from a five-fold excess to a five hundred-fold excess. Analysis of the conjugates (500×, 250×, 100×, 50×, 25×, 10×, and 5×), after reaction with the DTT reduced Ab, carried out via size exclusion chromatography as described immediately above in this example, indicated that the conjugates synthesized using a larger excess of linker had a smaller, narrower size distribution range (FIG. 20). However, there did not seem to be a large difference in the overall size distribution for the conjugates ranging from 5× to 100×. Tissue staining (tonsil, Ki-67, not shown) for each of these conjugates was roughly equivalent, where only 5× was slightly darker than other amounts.

Variation of HRP Concentration in Linker Coupling Reaction

Figure 21:
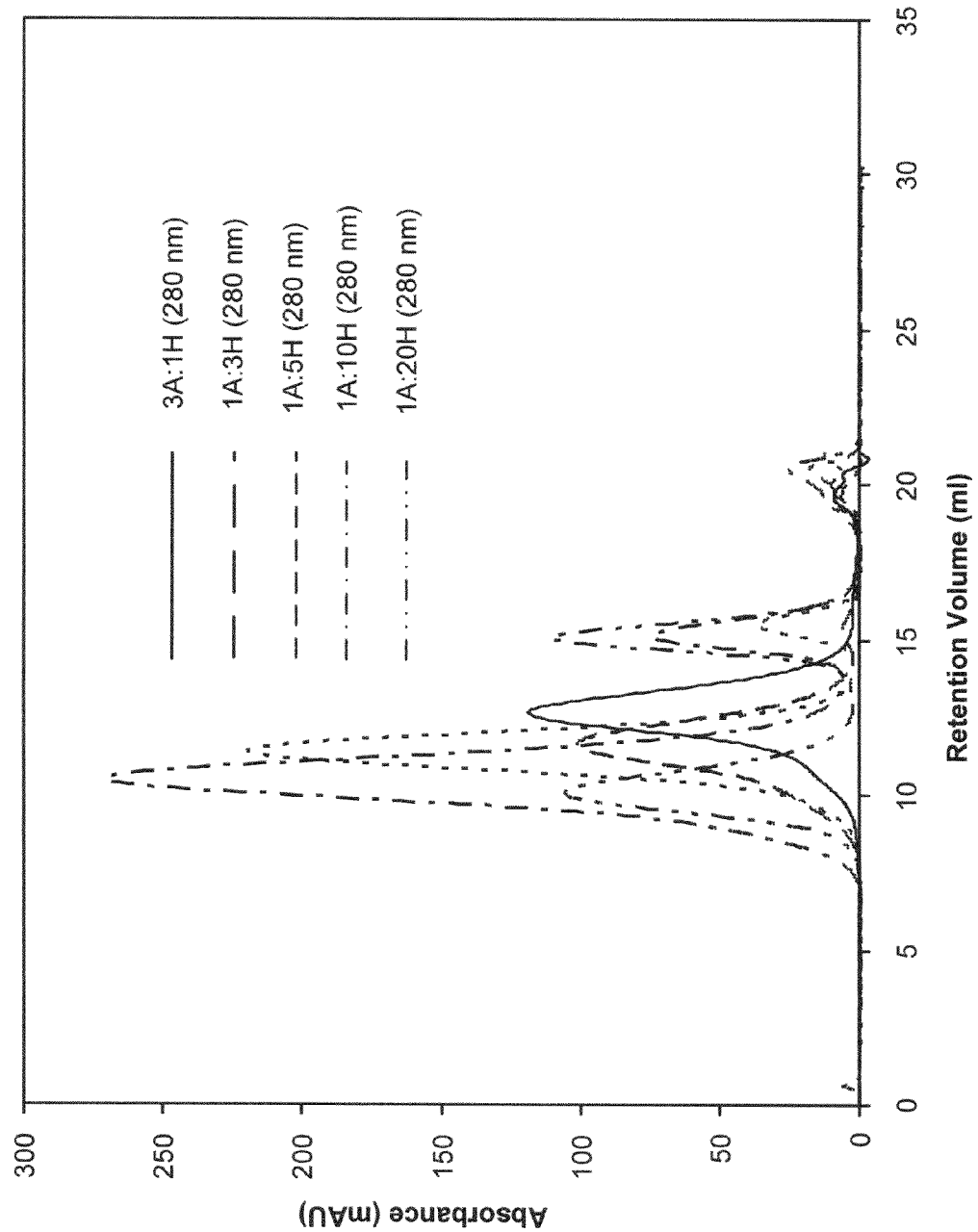
FIG. 21 is a size-exclusion chromatogram comparing the effect of variations of horseradish peroxidase concentrations on the MW profile of a disclosed conjugate.

Following the synthetic method outlined previously in example B, the effect of HRP concentration during the initial derivatization step was investigated. Stock solutions of HRP at the following concentrations: 5 mg/ml, 10 mg/ml, 15 mg/ml, 20 mg/ml, and 50 mg/ml, alongside the original protocol (25 mg/ml) concentration were used in the reactions. After the coupling step with the DTT-reduced antibody there was no difference in the overall size exclusion chromatograms for the synthesized conjugates (FIG. 21). In assaying the activity of the synthesized conjugates on tissue (tonsil, Ki-67), it was noticed that the staining specificity and intensity were identical for the conjugates synthesized using 5, 10, 15, 20, and 25 mg/ml HRP concentrations. However, the staining intensity decreased when the starting HRP concentration was increased to 50 mg/ml. It is concluded that the starting HRP concentration should stay between 10-25 mg/ml for the production level scale-up.

Variation of HRP/Ab Molar Ratios

Figure 22:
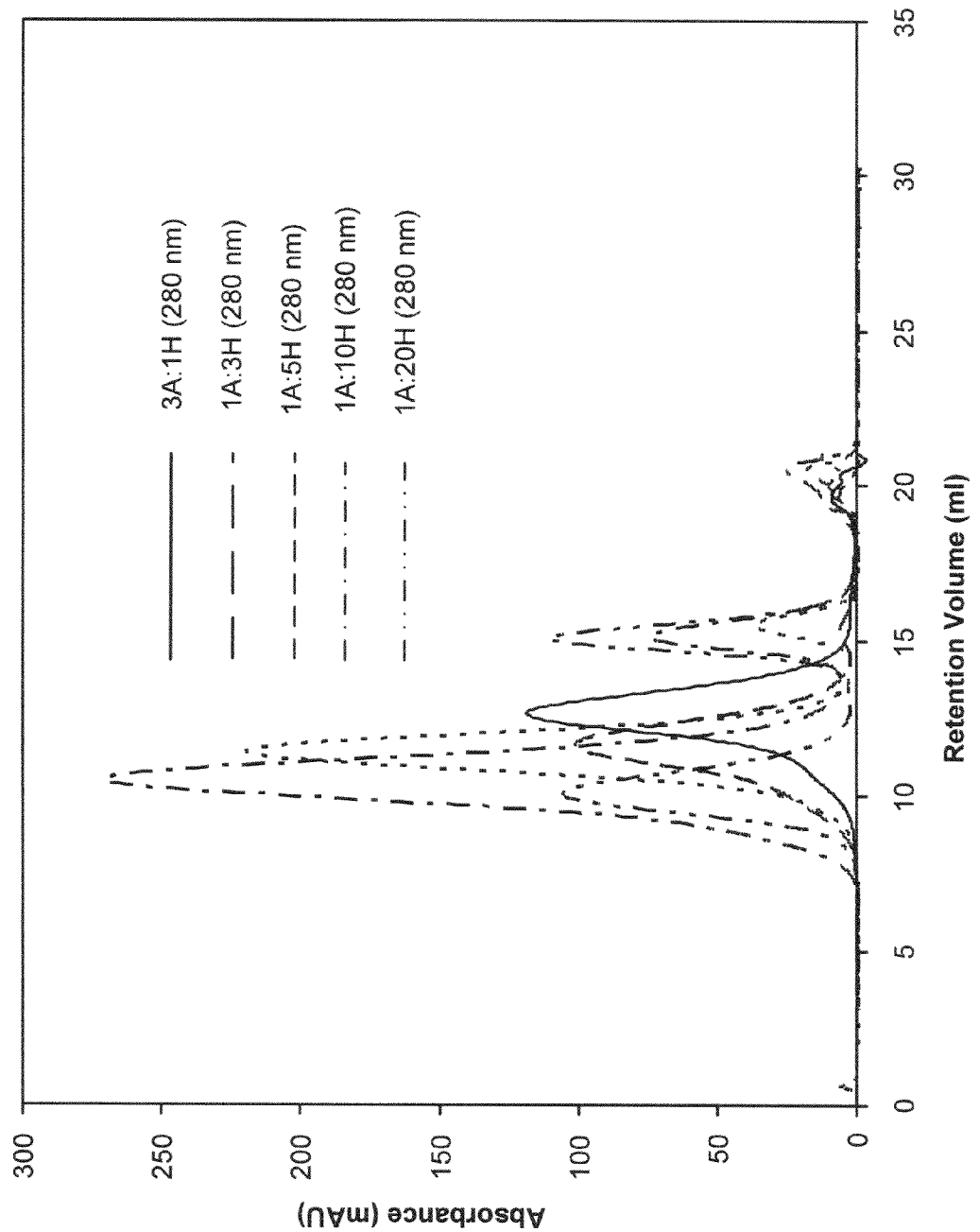
FIG. 22 is a size-exclusion chromatogram comparing the effect of variations of the ratio of antibody to horseradish peroxidase on the MW profile of a disclosed conjugate.

The HRP/IgG conjugates were synthesized using the protocol outlined in Example B, but the ratio of the DTT-reduced antibody to the maleimide derivatized HRP was varied. The following ratios (Antibody/HRP) were tested: 3:1, 1:3, 1:2, 1:4, 1:5, 1:10, 1:20, as well as the recommended 1:3. The profiles in the size exclusion chromatographs (FIG. 22) show that as the relative amount of HRP increases, so does the overall size of the conjugate, with the 1:20 (Ab:HRP) giving the largest conjugate and the 3:1 (Ab:HRP) generating the smallest. Each of these conjugates performed well on tissue (tonsil, Ki-67), with the 3:1 (Ab:HRP) producing the lightest amount of staining The 1:3 (Ab:HRP) is a midrange point with good staining and produces relatively high yields with respect to the HRP.

I. Preparation of a Rabbit Anti-Biotin-HRP-PEG12 Conjugate and its Use for Enzyme Metallographic In Situ Hybridization HRP-PEG$_{12}$-maleimide (4): To a 4 mL amber vial was added 18.4 mg (100 eq.) of MAL-dPEG$_{12}$™ NHS ester (Quanta Biodesign, Powell, Ohio, F.W.=865.92), followed by 341 uL (8.52 mg, 0.213 µM) of HRP (Horseradish Peroxidase, Pierce, Rockford, Ill.) as a 25 mg/mL solution in 0.1 M sodium phosphate, pH 7.5. The vial was then placed on an autorotator in the dark at ambient temperature (23-25° C.), and the amide bond forming reaction was allowed to proceed for 1 hour. A 340 µl aliquot was then removed for purification. (The capacity of the Akta Purifier injection loop utilized was 500 µl). Pure HRP-PEG$_{12}$-maleimide was then obtained by fractionating the sample on an Akta Purifier fitted with a Superdex 10/300 column eluted with 0.1 M sodium phosphate, pH 7.5 at 1.0 mL/min. The HRP containing fractions (F15-17) were pooled to give 1.5 ml of a 4.75 mg/mL solution of HRP-PEG$_{12}$-maleimide (83.6% recovery) as measured on an UV/VIS spectrophotometer using the extinction coefficient at 280 nm of a 1% solution at pH 7.5 of 6.52.

Rabbit Anti-Biotin Thiol (5): To a 4 mL amber vial was added 2.0 mL of Rabbit anti-Biotin (Bethyl, Montgomery Tex.) as a 1.0 mg/mL solution. To this solution was then added 105.2 µL of a freshly prepared 500 mM solution of the reducing agent DTT (1,4-Dithiothreitol). The vial was placed in the dark on an autorotator and the disulfide reduction was allowed to proceed for 25 minutes. The reaction solution was split into two equal volumes (due to the limited capacity of the desalting columns), and the excess DTT was removed by passing each of the for fractions across a PD-10 desalting column eluted with 0.1 M sodium phosphate, 1.0 mM EDTA, pH 6.5. The antibody containing fractions (F4-5) were combined to give 4.0 mL of a 0.436 mg/mL solution of DTT free Rabbit anti-Biotin-SH (87.5% recovery) as measured on a Agilent 8453 UV/VIS spectrophotometer using an extinction coefficient at 280 nm of a 1% solution at pH 6.5 of 14.

HRP-Antibody Conjugation (6): To the rabbit anti-biotin-IgG-thiol (5), was added a three fold molar excess of HRP-PEG$_{12}$-maleimide (4). The reaction was then incubated at ambient temperature (23-25° C.) overnight. After purification across a Superdex 200 10/300 GL SE column, 875 mg of conjugate with an average M.W. of 359 kD was obtained.

The enzyme metallographic procedure outlined in Example G was repeated using the PEG$_{12}$ anti-biotin conjugate as the primary antibody (i.e. no amplification), and resulted in surprisingly intense staining even though no amplification was employed. These results demonstrate that the use of long heterobifunctional PEG linkers (PEG$_8$ or greater, such as PEG$_{12}$ or greater) to prepare the disclosed conjugates surprisingly obviates the need for amplification schemes for IHC and ISH applications on tissue sections.

J. Maleimide/Hydrazide PEG-linker Synthesis

Scheme 6 shows a general method for preparing maleimide/hydrazide heterobifunctional PEG linkers. Briefly, a maleimide/active ester PEG linker (such as obtained from Quanta Biodesign) is reacted with a protected hydrazine derivative, and then reacted with acid to yield the maleimide/hydrazide PEG linker Scheme 6

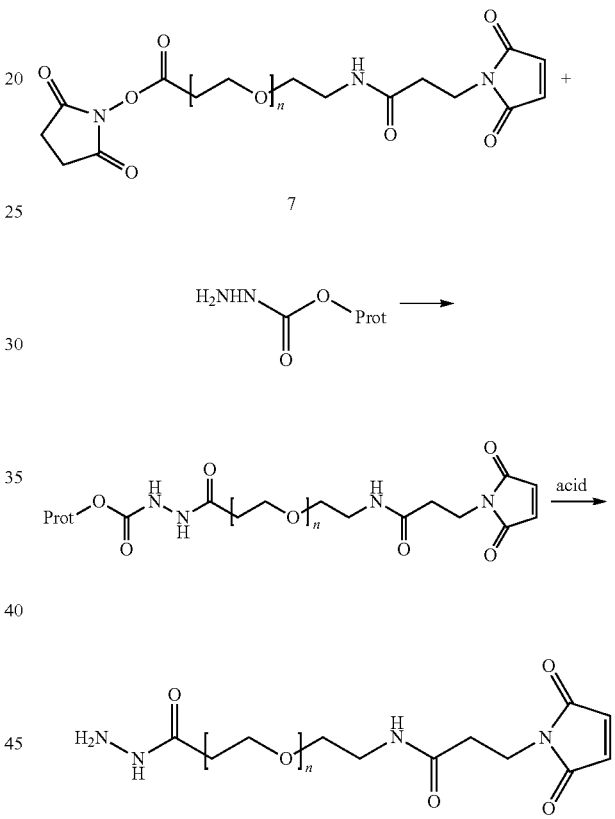

A specific synthesis of a maleimide/hydrazide PEG$_4$ linker is outlined in Scheme 7 below. To the active ester 7 (116 mg, 1.0 eq.) in 5 ml dry dioxane was added 30 mg (1.0 eq.) of the Boc protected hydrazine 8 in 5 ml of dry dioxane over 1 hour. The reaction was then stirred at ambient temperature under dry nitrogen for 16 hours. The reaction mixture was fractionated by HPLC utilizing a Waters Delta 600 HPLC fitted with a 2996 photo-diode array detector and a Phenomenex luna 10µ, C18(2), 100A, 250×30 mm column. The column was eluted with 30-60% ACN/water over 30 min at a flow rate of 12 mL/min. The desired Boc protected-PEG$_4$-maleimide 9 eluted at 38 minutes giving 50 mg of a thick yellow oil after drying under high vacuum. The final deprotected hydrazide 10 was then obtained by stirring the residue with 6 ml of anhydrous 2 NHCL/dioxane under dry nitrogen for 45 minutes. Concentration via rotory evaporation then gave 55 mg of the hydrazide-PEG$_4$-maleimide HCL salt.

Scheme 7

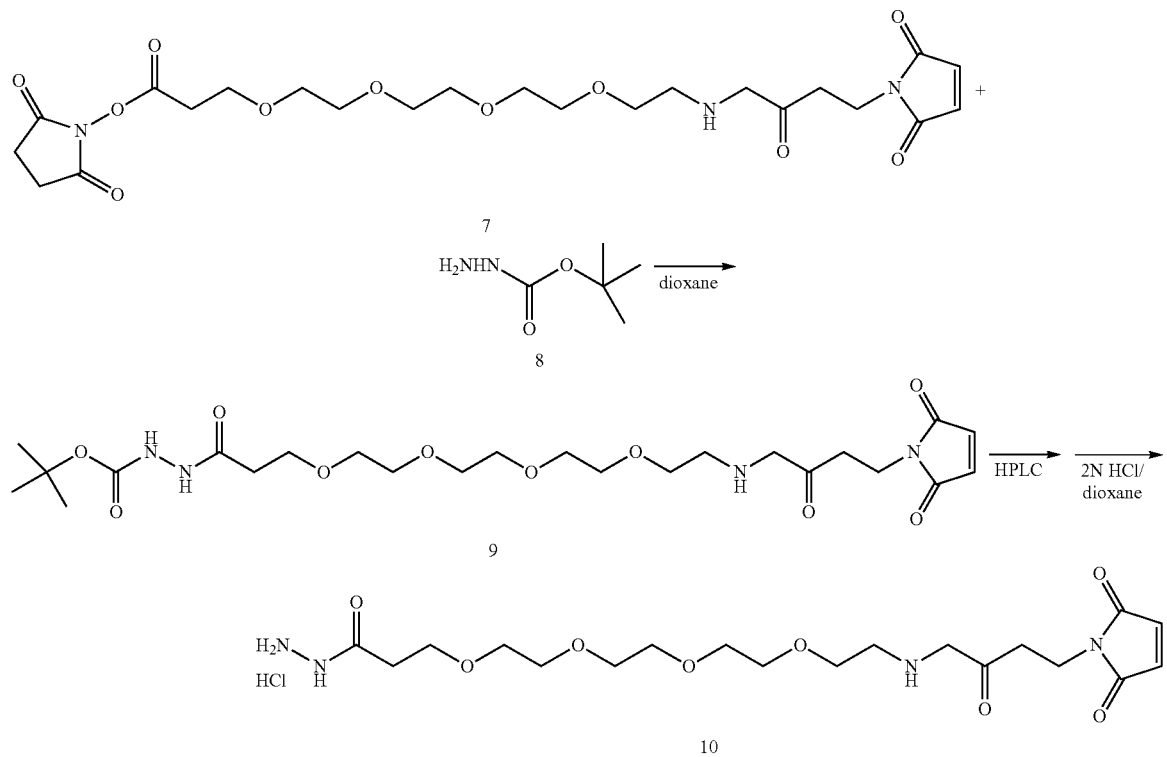

Although the principles of the present invention are described with reference to several embodiments, it should be apparent to those of ordinary skill in the art that the details of the embodiments may be modified without departing from such principles. The present invention includes all modifications, variations, and equivalents thereof as fall within the scope and spirit of the following claims.

We claim:

1. An antibody-PEG linker-enzyme signal-generating moiety conjugate, comprising:
   an antibody;
   a plurality of enzyme signal-generating moieties; and
   a plurality of monodisperse, heterobifunctional PEG linkers, wherein each enzyme signal-generating moiety is linked to the antibody through at least one of the plurality of monodisperse, heterobifunctional PEG linker to provide the antibody-PEG linker-enzyme signal-generating moiety conjugate having the formula

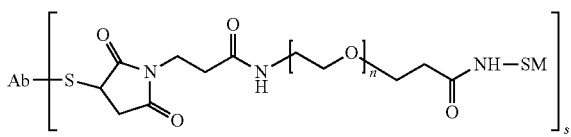

wherein Ab is the antibody, SM is the enzyme signal-generating moiety, n=4 to 12 and s=3 to 10.

2. The conjugate of claim 1, wherein SM is an oxidoreductase enzyme.

3. The conjugate of claim 1, wherein each SM independently is horseradish peroxidase, alkaline phosphatase, acid phosphatase, glucose oxidase, β-galactosidase, β-glucuronidase or β-lactamase.

4. The conjugate of claim 1, wherein each SM independently is horseradish peroxidase or alkaline phosphatase.

5. The conjugate of claim 1, wherein SM is alkaline phosphatase.

6. The conjugate of claim 1, wherein SM is horseradish peroxidase.

7. The conjugate of claim 1, wherein the antibody comprises an anti-antibody antibody.

8. The conjugate of claim 7, wherein the anti-antibody antibody is an anti-IgG antibody.

9. The conjugate of claim 1, wherein the antibody comprises an anti-hapten antibody.

10. The conjugate of claim 1, wherein s=3 to 6.

11. The conjugate of claim 10, wherein s=3 to 4.

12. The conjugate of claim 11, wherein SM is horseradish peroxidase or alkaline phosphatase.

* * * * *